United States Patent [19]

Zamost et al.

[11] Patent Number: 5,491,087
[45] Date of Patent: Feb. 13, 1996

[54] **THERMOSTABLE ARABINO FURANOSIDE PRODUCED BY *BACILLUS STEAROTHERMOPHILUS* NRRL B-18659, *BACILLUS STEAROTHERMOPHILUS* NRRL B-18660 AND *BACILLUS STEAROTHERMOPHILUS* NRRL B-18661**

[75] Inventors: Bruce L. Zamost, Danbury; Dana D. Elm, Waterbury, both of Conn.

[73] Assignee: Novo Nordisk A/S, Bagsvaerd, Denmark

[21] Appl. No.: 418,044

[22] Filed: Apr. 6, 1995

Related U.S. Application Data

[62] Division of Ser. No. 87,476, Jul. 2, 1993, abandoned, which is a continuation of Ser. No. 961,044, Oct. 14, 1992, abandoned, which is a continuation of Ser. No. 535,099, Jun. 8, 1990, abandoned.

[51] Int. Cl.⁶ .............................. C12N 9/24; C12N 1/20; C12N 1/00; D21C 3/00
[52] U.S. Cl. ........................ 435/200; 435/832; 435/278; 435/252.5
[58] Field of Search .............................. 435/200, 252.31, 435/832, 278, 252.5

[56] References Cited

U.S. PATENT DOCUMENTS

| | | | |
|---|---|---|---|
| 4,771,003 | 9/1988 | Stellwag et al. | 435/221 |
| 5,010,008 | 4/1991 | Brumm | 435/202 |
| 5,434,071 | 7/1995 | Rosenberg et al. | 435/200 |

FOREIGN PATENT DOCUMENTS

| | | | |
|---|---|---|---|
| 0029976 | 11/1980 | European Pat. Off. | |
| 1252280 | 10/1989 | Japan | 435/209 |
| 1252281 | 10/1989 | Japan | 435/209 |

OTHER PUBLICATIONS

JP 1063377, abstract (1989).
Methods in Enzymology, vol. 160, pp. 655–659 (1988).
Kang et al., *Korean J. Appl. Microbiol. Bioeng.*, 14, 1986, 447–453.

Poutaney et al., *Appl. Microbiol. Biotechnol.*, 28, 1988, 425–432.

Uchino, F., "A Thermostable Xylanase from a Thermophilic Acidophilic *Bacillus sp*", *Agric. Biol. Chem.*, 45 (5), pp. 1121–1127, 1981.

Okazaki, W. et al., "Purification and Characterization of Xylanases from Alkalophilic Thermophilic *Bacillus* spp.", *Agric. Biol Chem.*, 49 (7) pp. 2033–2039, 1985.

Okazaki, W. et al., "Production and Properties of two types of xylanases from Alkalophilic thermophilic *Bacillus* spp.", *Applied Microbiology and Biotechnology*, 19, pp. 335–340, 1984.

Grüninger, H. et al., "A Novel, Highly Thermostable D–xylanase," Enzyme Microb. Technol., vol. 8, pp. 309–314 1986.

McCarthy, A. J. et al., "Studies on the Extracellular Xylanase Activity of Some Thermophilic Actinonycles", *Appl. Microbiol. Biotech.* 21, pp. 238–244 1985.

*Primary Examiner*—David M. Naff
*Assistant Examiner*—Michael V. Meller
*Attorney, Agent, or Firm*—Steve T. Zelson; Cheryl H. Agris

[57] ABSTRACT

An isolated arabinofuranosidase from *Bacillus stearothermophilus* NRRL B-18659, *Bacillus stearothermophilus* NRRL B-18660 and *Bacillus stearothermophilus* NRRL B-18661 is disclosed. The arabinofuranosidase has a maximum activity at about pH 6.0 and at about 65° C., maintains at least about 50% of its maximum activity at 70° C. and pH 7.0 after 80 minutes, and has an isoelectric point of about 4.4. The arabinfuranosidase can be used in a method of hydrolyzing xylan present in wood pulp at temperatures of at least about 60° C. and a pH of at least about 7.0. The arabinofuranosidase is used along with at least two xylanases and a xylosidase isolated from the above *Bacillus stearothermophilus* strains.

4 Claims, 27 Drawing Sheets

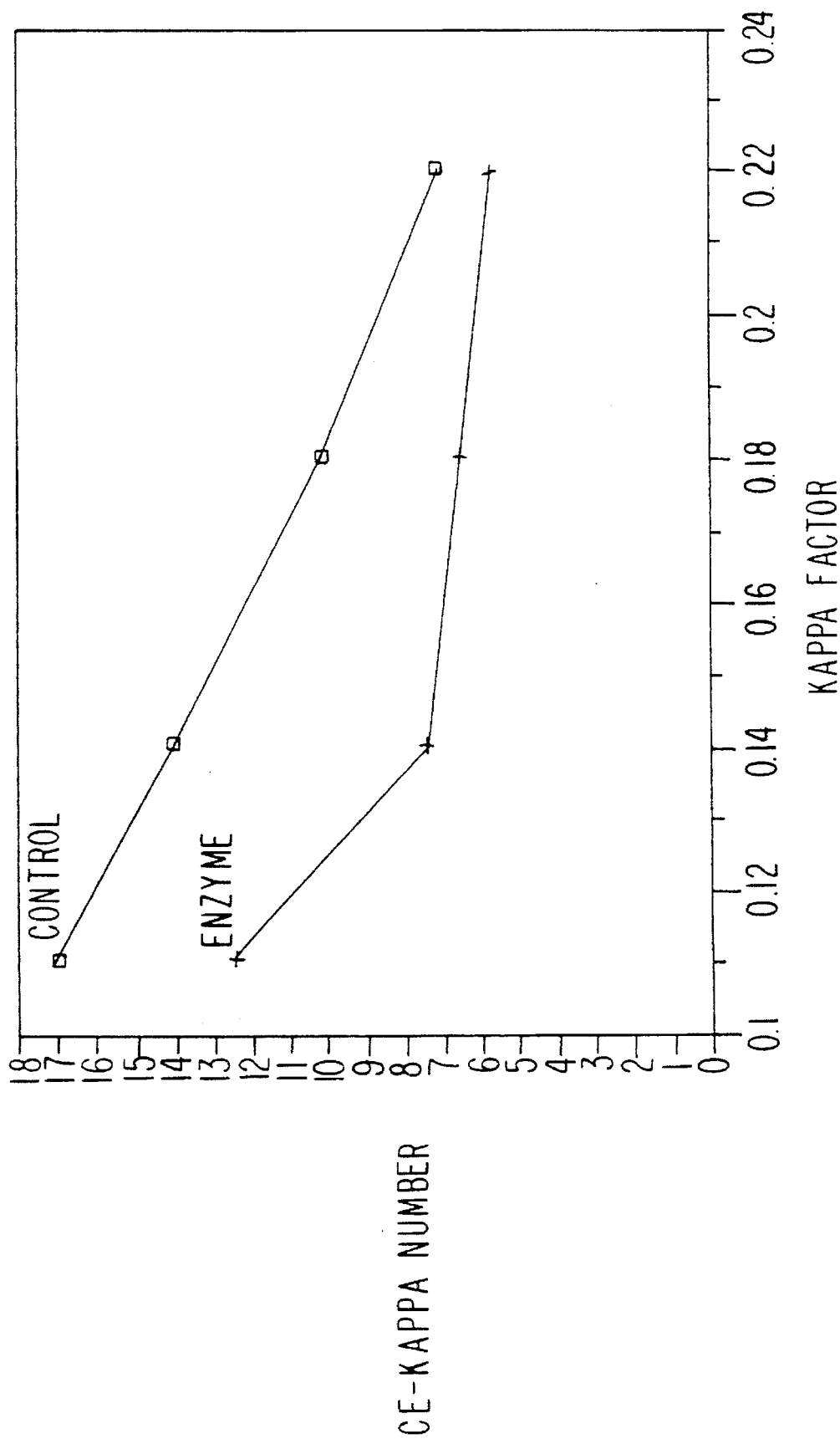

THERMOSTABLE ARABINO FURANOSIDE PRODUCED BY *BACILLUS STEAROTHERMOPHILUS* NRRL B-18659, *BACILLUS STEAROTHERMOPHILUS* NRRL B-18660 AND *BACILLUS STEAROTHERMOPHILUS* NRRL B-18661

This is divisional application of application Ser. No. 08/087,476 filed Jul. 2, 1993, now abandoned, which is a continuation of 07/961,044 filed Oct. 14, 1992, now abandoned, which is a continuation of application Ser. No. 07/535,099 filed Jun. 8, 1990, now abandoned, the contents of which are incorporated herein by reference in their entirety.

1.0 BACKGROUND OF INVENTION

Xylan, a major component of plant hemicellulose, is a polymer of D-xylose linked by B-1,4-xylosidic bonds. Xylan can be degraded to xylose and xylo-oligomers by acid or enzymatic hydrolysis. Enzymatic hydrolysis of xylan produces free sugars without the by-products formed with acid (e.g. furans).

There are currently four major applications for xylanses; 1) enzymatic breakdown of agricultural wastes for production of alcohol fuels; 2) enzymatic treatment of animal feeds to release free pentose sugars; 3) manufacturing of dissolving pulps yielding cellulose; and 4) bio-bleaching of wood pulps. [Detroym R. W. In: *Organic Chemicals from Biomass*, (CRC Press, Boca Raton, Fla., 1981) 19–41.; Paice, M. G., and L. Jurasek. *J. Wood Chem. Technol.* 4: 187–198.; Pommier, J. C., J. L. Fuentes, G. Goma. *Tappi Journal* (1989): 187–191.; Senior, D. J., et al., *Biotechnol. Letters* 10 (1988):907–912.]

The pulp and paper industry is using xylanase compositions in the bio-bleaching process to enhance the brightness of bleached pulps, to decrease the amount of chlorine used in the bleaching stages, and to increase the freeness of pulps in the recycled paper process. [Eriksson, K. E. L., *Wood Science and Technology* 24 (1990); 79–101.; Paice, M. G., R. Bernier, and L. Jurasek, *Biotechnol. and Bioeng.* 32 (1988): 235–239.; Pommier, J. C., J. L. Fuentes, and G. Goma, *Tappi Journal* (1989): 187–191.]

Kraft pulping, a process widely used in the pulp and paper industry, involves the alkaline sulfate cooking of pulp to remove 95% of the lignin. The remaining 5% of lignin gives the pulp a dark brown color which has the tendency to darken in UV light or by oxidation. In order to obtain a white pulp for high quality paper, the brown color is removed by a multi-stage bleaching process using chlorine and/or chlorine dioxide.

Presently, there is much concern about the environmental impact of the chemicals generated from the bleaching process. Enzymes can aid in the removal of lignin from the pulp without any harmful side products. Reports show that lignin in wood is linked to xylan, possibly through an arabinose side chain. [Eriksson, O., et al., *Wood Sci.Technol.* 14 (1980); 267.; Takashi, N., and T. Koshijiima, *Wood Sci.Technol.* 22 (1988); 177–189]. By hydrolyzing the xylose-xylose bonds (xylanase, xylosidase) and arabinose-xylose bonds (arabinofuranosidase), a greater release of lignin occurs during bleaching. Thus, by enzymatically treating the pulp prior to bleaching the amount of active chlorine needed would in turn decrease. [Viikari, L., et al., *Proceedings of the 3rd International Symposium on Biotechnology in the Pulp and Paper Industry* (1986); 67.]

1.1 Xylanases

The current results in literature have been obtained using fungal preparations from *Trichoderma* [Paice, M. G., L. Jurasek, *J. Wood Chem. Technol.* 4 (1989): 187–198.; Senior, D. J., et al., *Biotechnol. Letters.* 10 (1988): 907–912.] which require pH adjustment of the wood pulps below pH 6.0. These fungal preps also have low thermostability requiring the biobleaching to be performed at a temperature below 55° C. and for incubation periods up to 24 hours.

Neutral xylanases from obligate alkalophilic, thermostable *Bacillus* spp. have been described. [Okazaki, W., T. Akiba, K. Horikoshi, and R. Akahoshi, *Appl. Microbiol. Biotechnol.* 19 (1984): 335–340.] Bacillus isolates W1, W2, W3, and W4 all grow between 40°–50° C. and at a pH above 9.0. The strains reportedly produced two types of neutral xylanases—enzyme I with a pH optimum of 6.0 and a temperature optimum of 65° C., and enzyme II with a temperature optimum of 70° C. and a pH optimum of 7.0.

The enzymes from W1 and W2 were further characterized [Akiba, T., K. Horikoshi, *Methods in Enzymology* 160 (1988): 655–659.; Okazaki, W. T., T. Akiba, K. Horikoshi, and R. Akahoshi, *Agr. Biol. Chem.* 49 (1985): 2033–2039.] and reportedly show the following properties. Enzyme II, from strain W1, is said to have a pH optimum of 7.0, a temperature optimum of 70° C., and 20% activity at pH 10.5. The enzyme reportedly retains 30% activity after 1 hour at 45° C., pH 10.5. Enzyme II, from strain W2, has a similar pH and temperature optimum but is slightly more active at pH 10.5 (30% vs. 20%) and more thermostable (40% activity after 1 hour at pH 10.5, 45° C.) than enzyme II from strain W1.

A thermostable xylanase produced by a "*Bacillus stearothermophilus*-like" strain has been described. [Gruninger, H., and A. Fiechter, *Enzyme Micro. Technol.* 8 (1986): 309–314.] Strain 4125 reportedly produces a neutral xylanase with a pH optimum of 6.5–7.5 (but only 65% activity at pH 9.5), a temperature optimum of 75° C., and a half-life of 15 hours at 75° C. No description of activity past pH 9.5 was reported in this reference. Strain 4125 has not been identified by any known culture collections as a *B. stearothermophilus* isolate, and no taxonomic data was given. The strain is not available from any collection or from the authors.

Kang, et al. described another xylanase from an alkalophilic, thermophilic *Bacillus* sp. [Kang, I. S., N. K. Sung, H. K. Chun, T. Akiba, and K. Horikoshi, *Korean J. Appl. Microbiol. Bioeng.* 14 (1986): 447–453.] The enzyme from this *Bacillus* strain, K-17, was also reportedly shown to have two components. Xylanase I from K-17 has optimal activity between pH 7.0–8.0 and 65° C. It has no activity at pH 10.5. Xylanase II from K-17 is said to have 20% of its optimal activity at pH 10.5 and retains 70% activity after 1 hour at 65° C., pH 6.5.

For biobleaching, an alkaline-active, thermostable xylanase composition would be advantageous due to the high pH and temperature of a wood pulp stream produced during the Kraft process. By addition of the enzyme, especially after the first wash step, the generation of environmentally harmful chemicals, such as dioxins, could be significantly reduced.

1.2 Xylosidases

The use of Beta-xylosidase to increase the yield of xylose during xylan hydrolysis has been well documented. [Poutanen, K., and J. Puls, *Appl. Microbiol. Biotechnol.* 28 (1988): 425–432.] The main drawback to the xylosidases described in literature is their end-product inhibition. The xylosidase from the well studied xylanase composition produced by *Trichoderma reesei* is inhibited by low levels of xylose, which ultimately limits the extent of hydrolysis. The *T. reesei* xylosidase shows over 50% inhibition in the presence of 300 mM xylose and is over 80% inhibited by the presence of 500 mM xylose.

An extracellular xylosidase has been described for *Bacillus* strain K-17 described by Kang, et al. The xylosidase has an optimal activity at pH 7.0 and at 45° C. The enzyme is not thermostable, being completely inactivated after 10 minutes at 60° C.

One object of this invention is to provide an enzymatic means to increase the yield of xylose during xylan hydrolysis which is achieved by using a xylosidase that is not inhibited by the end products of its action.

1.3 Arabinofuranosidases

Arabinofuranosidases are capable of hydrolyzing both 1,3 and 1,5 alpha-L-arabinofuranosyl linkages and are capable of removing arabinose units from the nonreducing end of an arabinan chain. [Kaji, A., *Advances Carbohydr. Chem. Biochem.* 42 (1984): 383–394.] Studies on lignin-carbohydrate bonds in wood have indicated that xylan is associated with lignin through arabinose side chains. [Takashi, N., and Koshijima, *Wood Sci. And Technol.* 22 (1988): 177–189.; Eriksson, O., D. A. Goring, and B. O. Lindgren, *Wood Sci. Technol.* 14 (1980): 267.] Cleavage of these arabinofuranosyl bonds has been postulated to aid in the removal of lignin from wood pulp. [Biely, P., *Trends in Biotechnol.* 3 (1985): 286–290.]

Numerous microbial arabinofuranosidases from *Bacillus* spp. other than *B. stearothermophilus* have been studied and reported. [Karimi, S., and O. P. Ward. *Journal of Industrial Microbiology* 4 (1989): 173–180.] None of the non-thermophilic *Bacilli* described by Karimi and Ward produced high temperature active, thermostable arabinofuranosidases.

2.0 SUMMARY OF THE INVENTION

The invention herein comprises strains of microorganisms that produce a heat and alkaline stable xylanase composition that is active in the pH range between 5.0 and 11.0 and at temperatures between 40°–80° C. The enzyme composition is able to selectively solubilize the hemicellulose fraction of wood pulp without destruction of the cellulosic structure (due to the lack of cellulase production) and is useful in the enzymatic treatment of wood pulps to increase brightness and decrease chlorine load.

Isolate BPS-3, which has been identified by the Deutsche Sammlung Von Mikroorganismen (DSM) as *Bacillus stearothermophilus,* produces an extracellular xylanase composition when grown on xylan, hydrolyzed starch or a mixture of the two substrates. The enzyme composition consists of at least two endoxylanases, a beta-xylosidase, and an alpha-arabinofuranosidase.

Isolates BPS-3-H-17-4 and BPS-3-X2 are asporogenous mutants derived from BPS-3 after mutagenesis with ethylmethanesulfonate. They both produce the enzyme composition and are incapable of forming a terminal endospore.

Isolate 243-7-1, identified by DSM as a *B. stearothermophilus,* also produces an alkaline-active xylanase composition when grown on xylan or hemicellulose containing substrates.

The pH profile of the xylanase composition from BPS-3 shows a pH optimum between pH 7.0–7.5 and exhibits 50% activity at pH 11.0 and 60° C. Eighty-five percent of BPS-3 enzyme activity remains at pH 9.5.

The enzyme from BPS-3 is also alkaline-active having 60% activity at pH 10.5. The BPS-3 enzyme is thermostable, retaining over 80% activity after 3 hours at 65° C., pH 10.5.

In addition, the BPS-3 xylanase shows no loss of activity after 3 hours at 65° C., pH 7.0.

The beta-xylosidase from BPS-3 is novel in respect to temperature optimum, thermostability, and resistance to end-product inhibition. The BPS-3 xylosidase has a temperature optimum of 75° C. at pH 6.0, and retains over 60% activity after 4 hours at 65° C., pH 7.0. The xylosidase from BPS-3 shows only 25% inhibition in the presence of 900 mM xylose (FIG. 2).

This invention also discloses an arabinofuranosidase capable of hydrolyzing both 1,3 and 1,5 alpha-L-arabinofuranosyl linkages and capable of removing arabinose units from the nonreducing end of an arabinose chain. The arabinofuranosidase is also a novel enzyme. In addition, the literature does not contain any reference for an arabinofuranosidase from a thermophilic *Bacillus.*

3.0 BRIEF DESCRIPTION OF THE FIGURES

Figure 4:
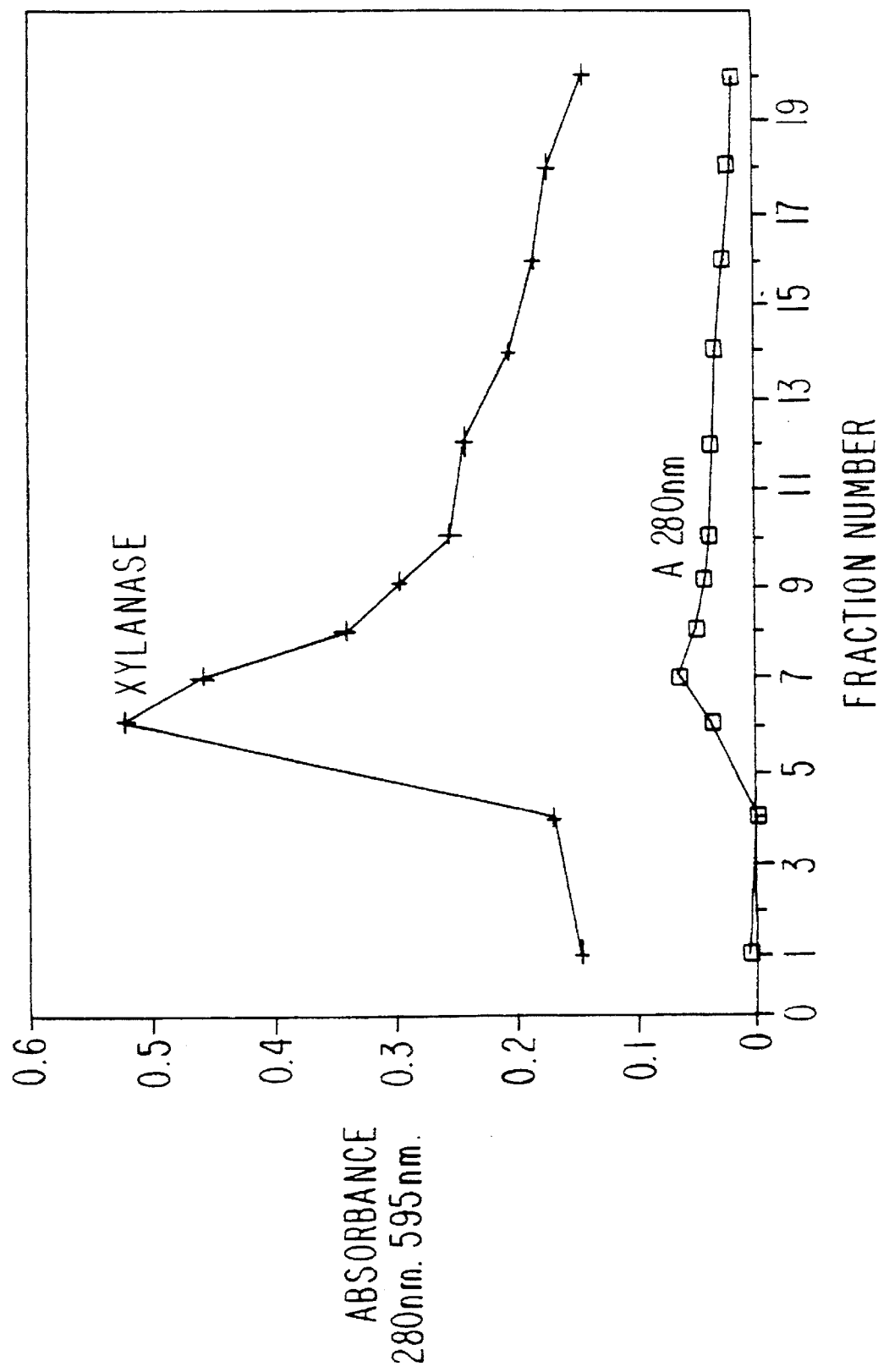

FIG. 4 provides an Ion-Exchange Chromatogram—Flow through.

Figure 5:
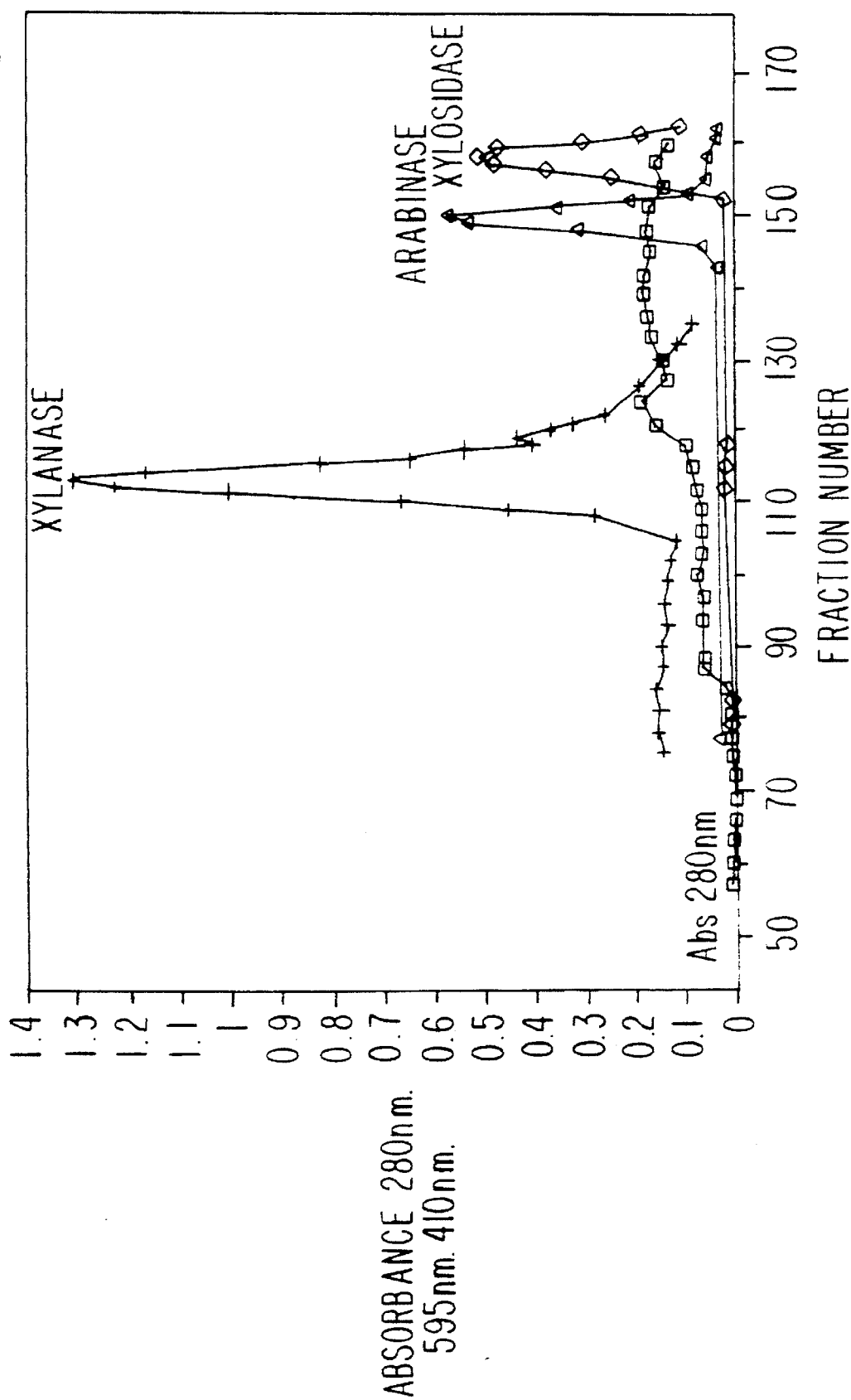

FIG. 5 provides an Ion-Exchange Chromatogram—Gradient.

Figure 6:
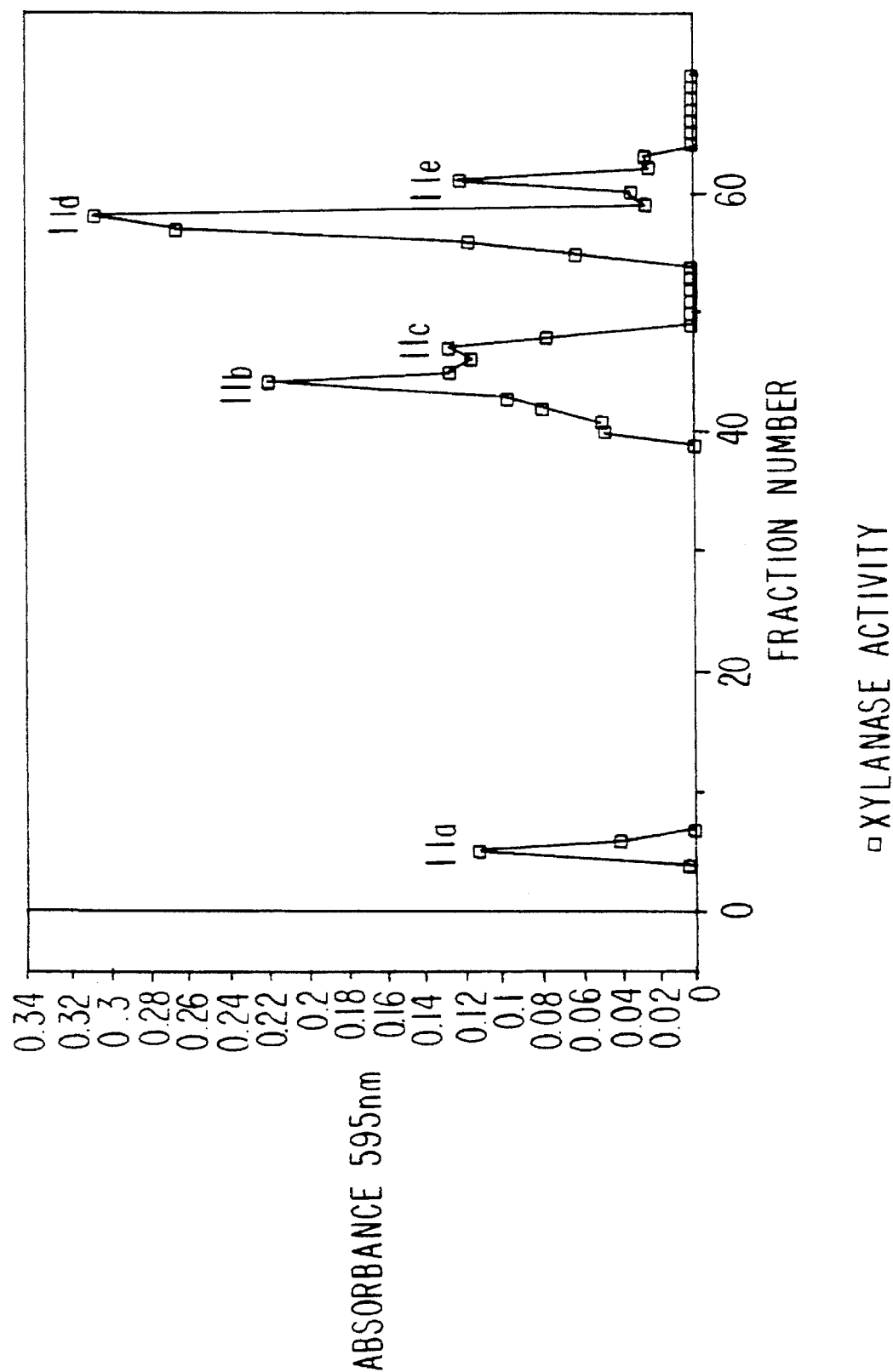

FIG. 6 provides an Chromatofocusing Chromatogram.

Figure 7:
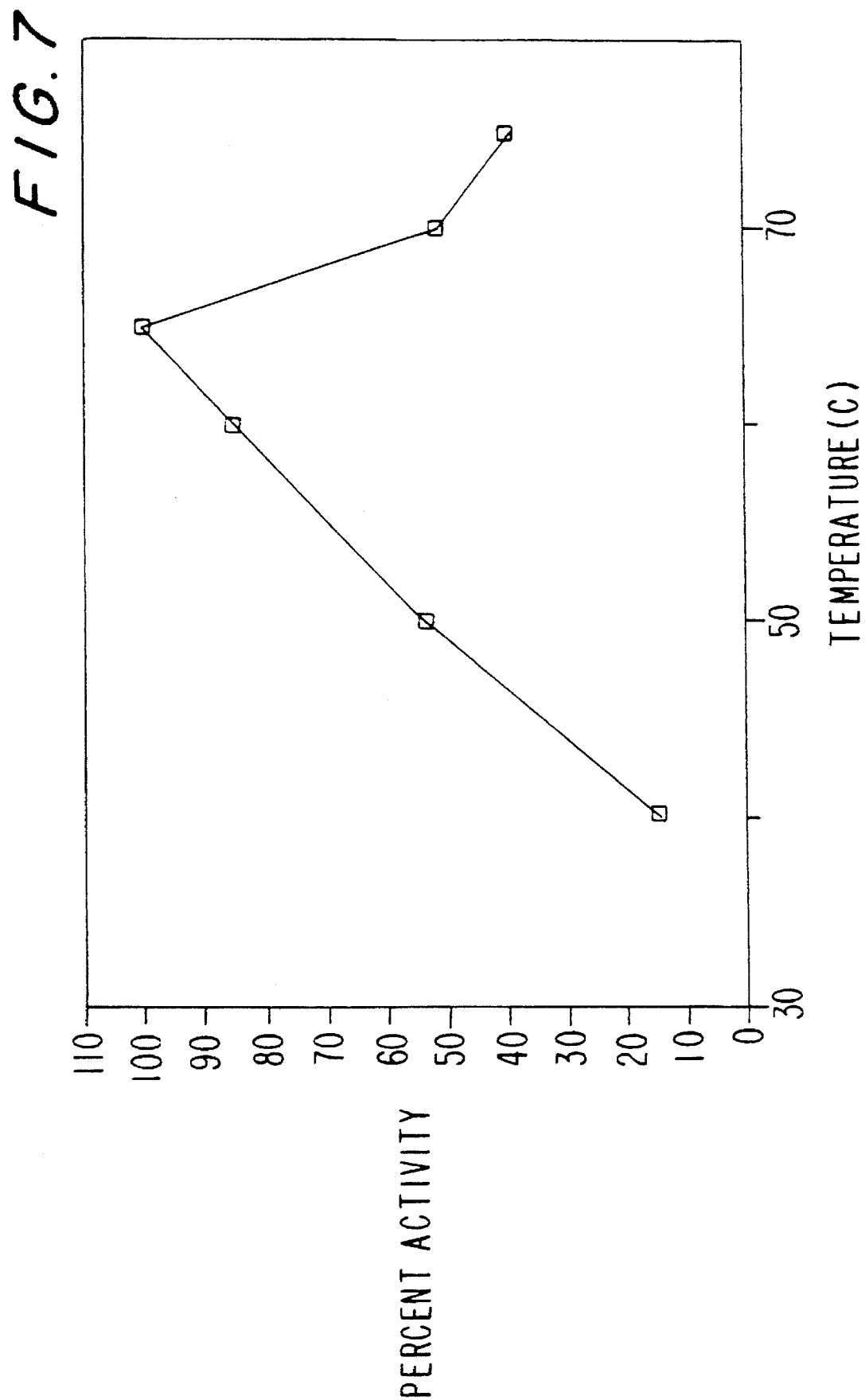

FIG. 7 shows the Temperature Profile of Crude Xylanase.

Figure 8:
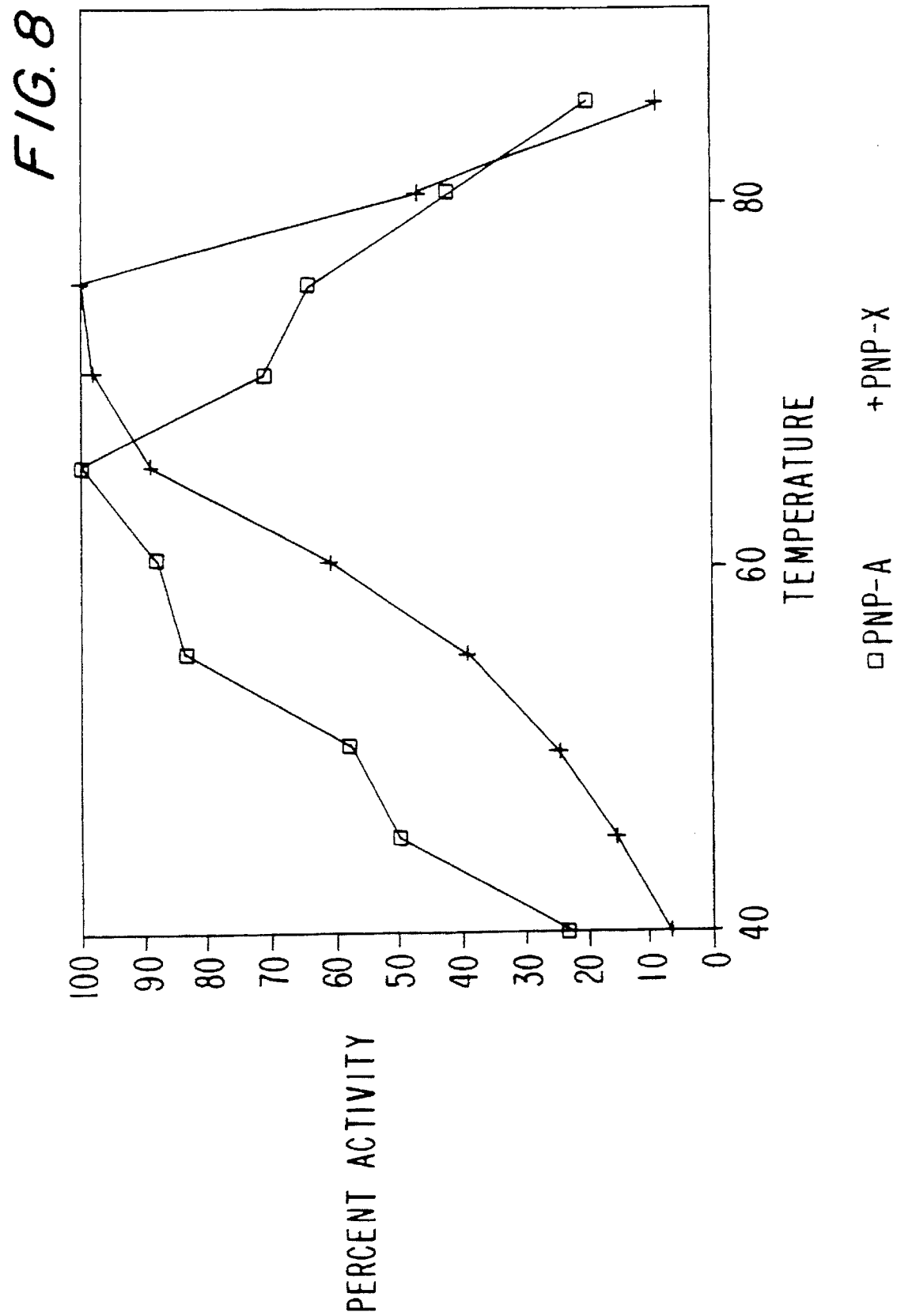

FIG. 8 shows the Temperature Profile of Xylosidase and Arabinofuranosidase.

Figure 9:
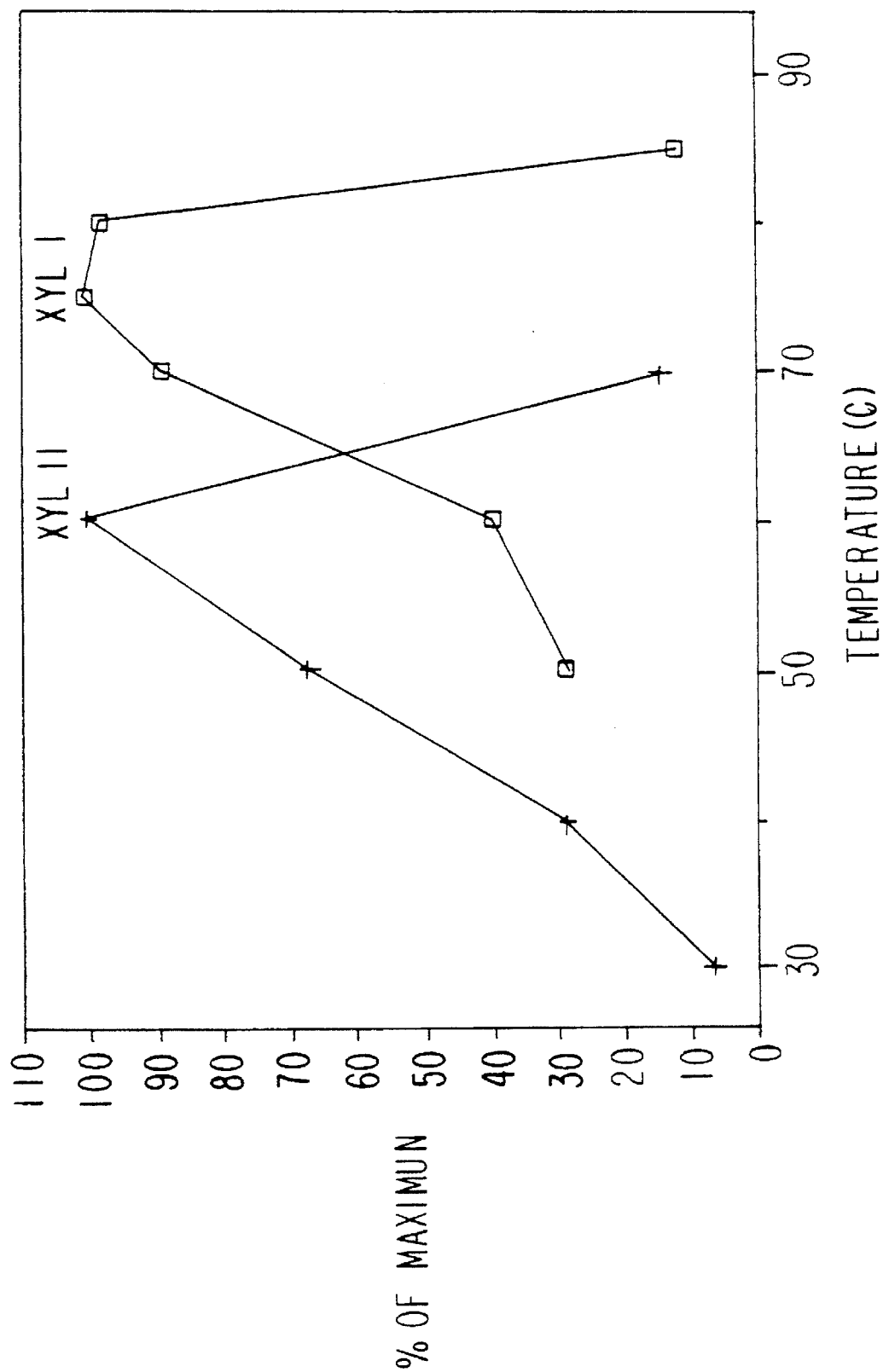

FIG. 9 shows the Temperature Profile of Xylanase I & Xylanase II.

Figure 10:
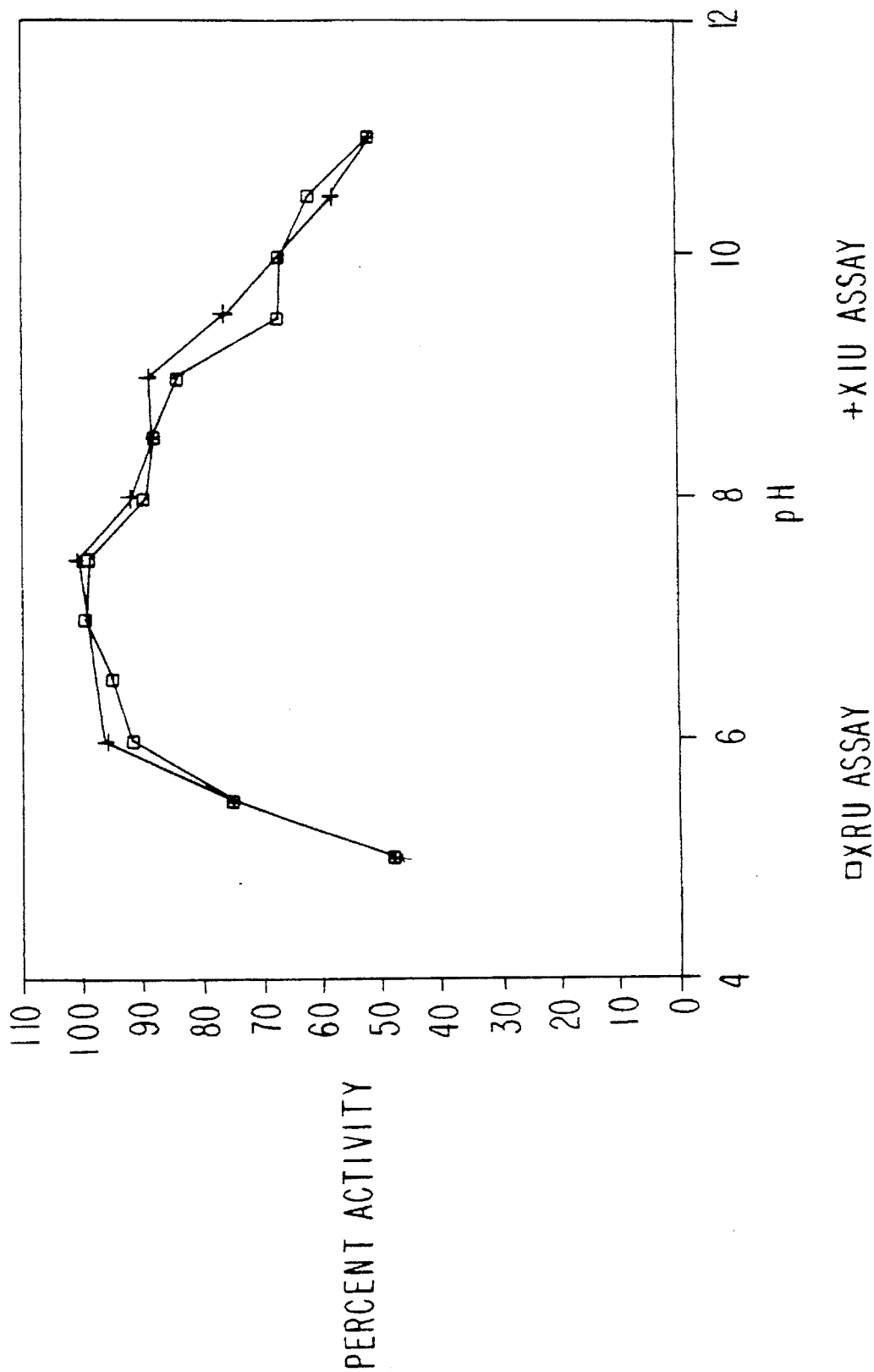

FIG. 10 illustrates the pH Profile of Crude Xylanase.

Figure 11:
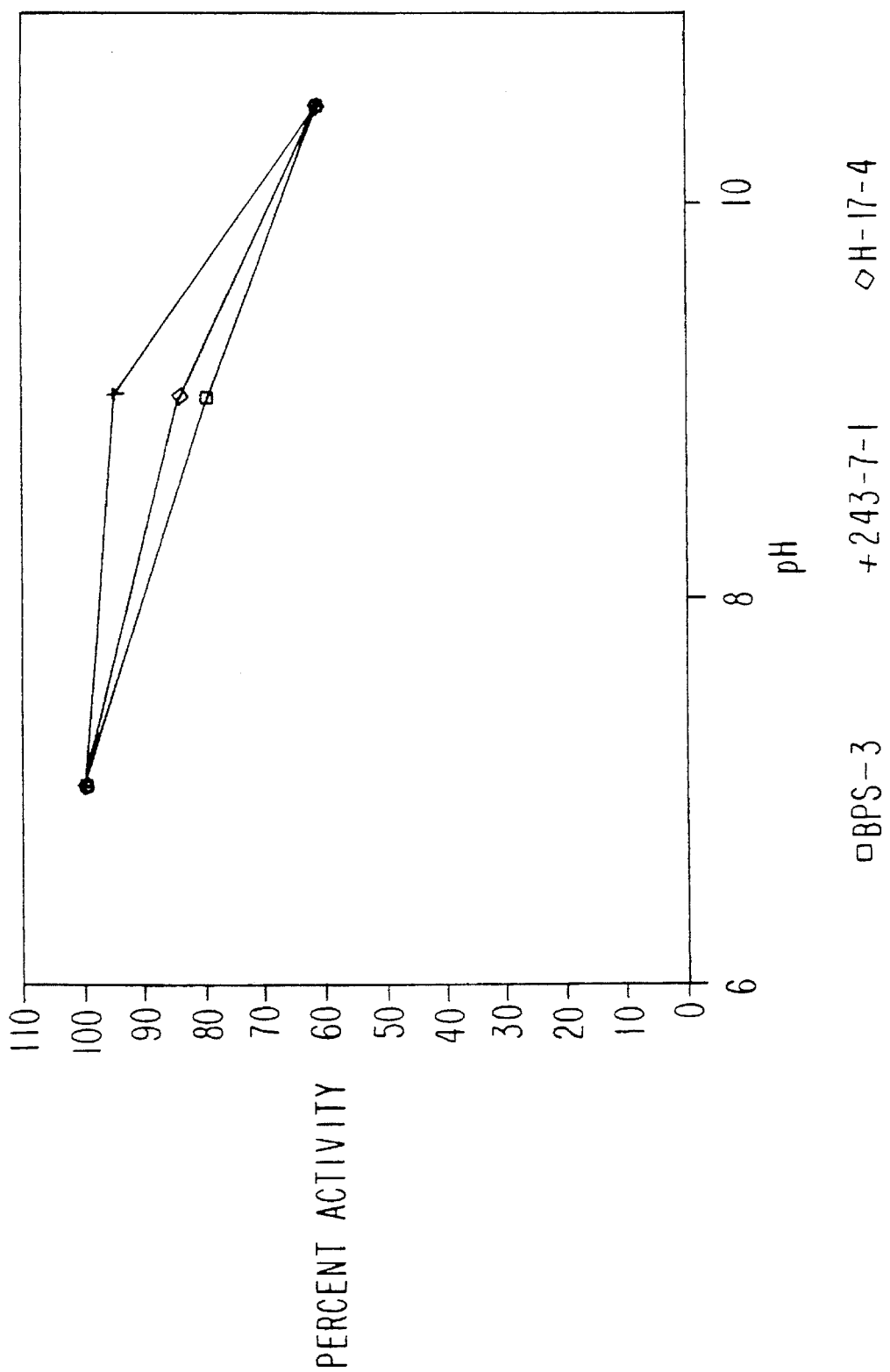

FIG. 11 illustrates the pH Profile of Xylanase Producing Strains.

Figure 12:
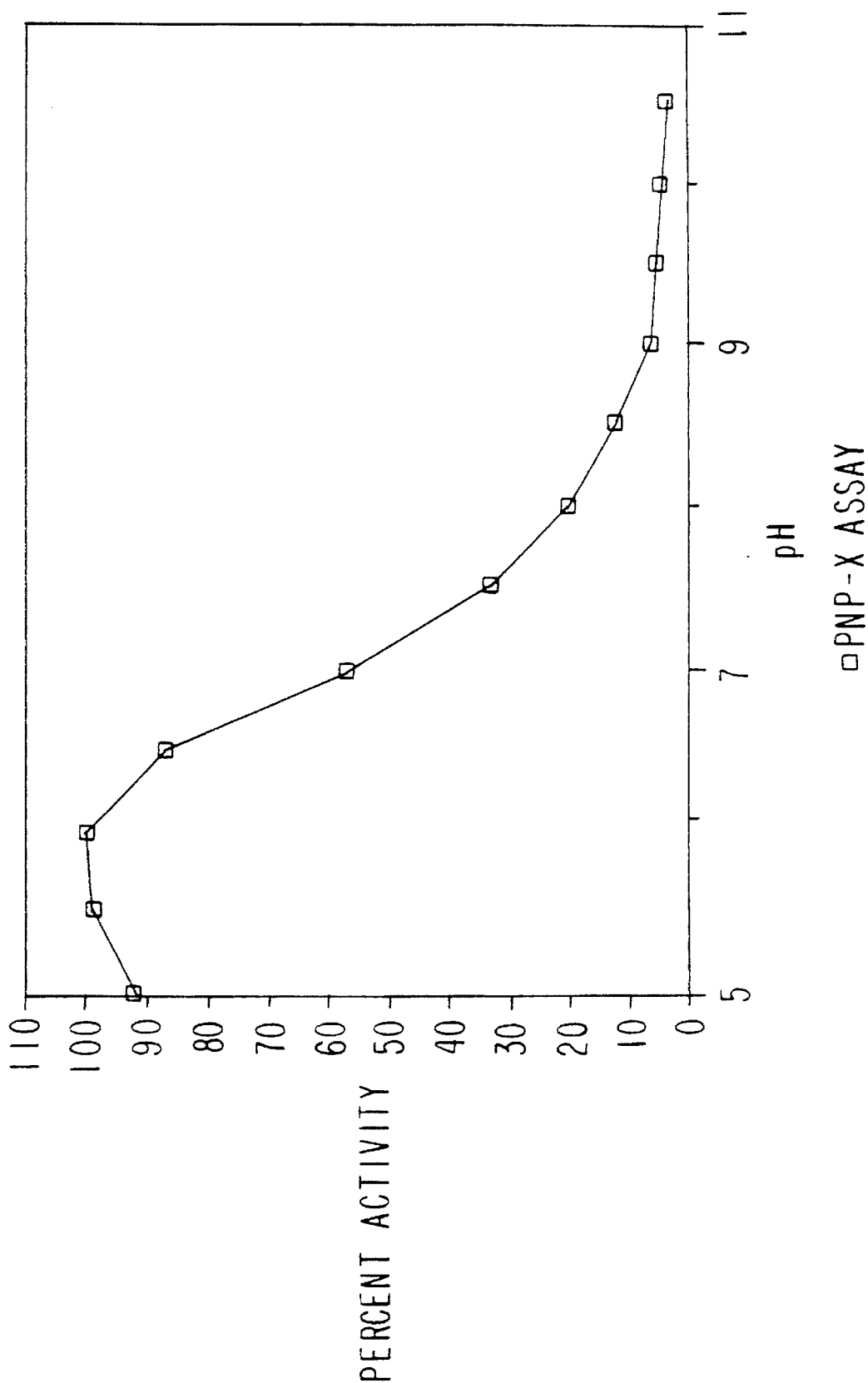

FIG. 12 shows the pH Profile of Xylosidase.

Figure 13:
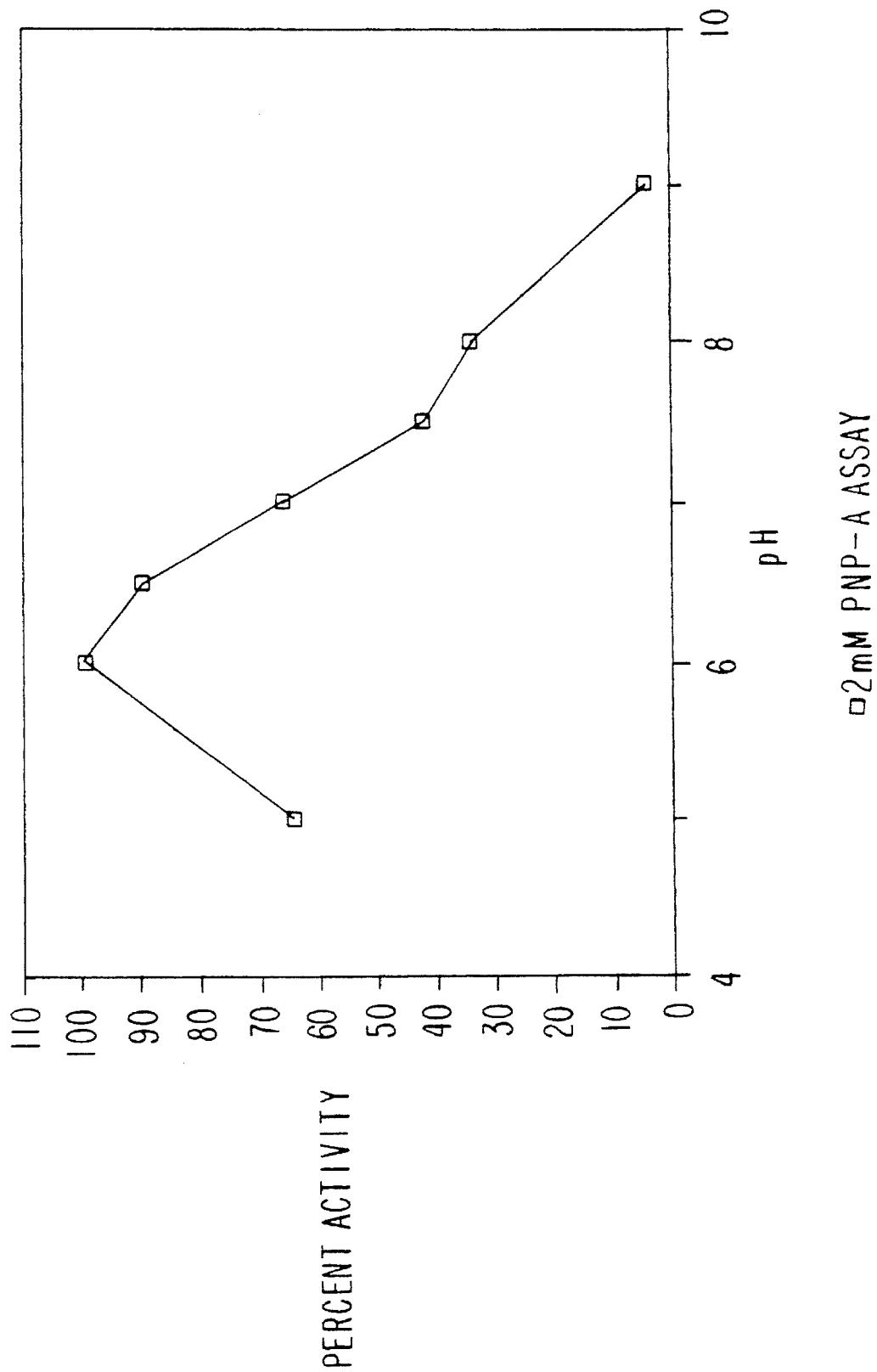

FIG. 13 shows the pH Profile of Arabinofuranosidase.

Figure 14:
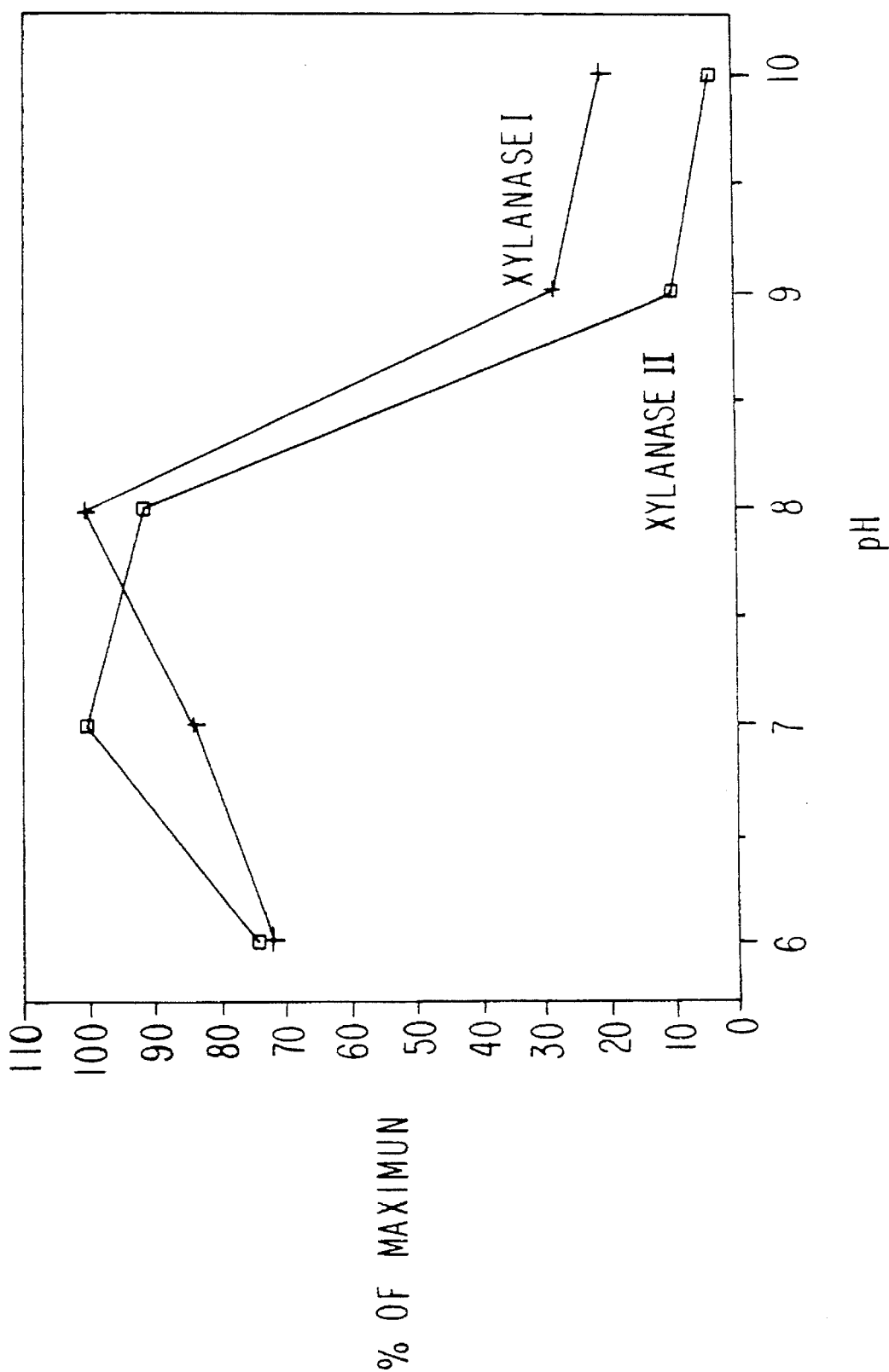

FIG. 14 provides a pH Profile of Xylanase I and Xylanase II.

Figure 15:
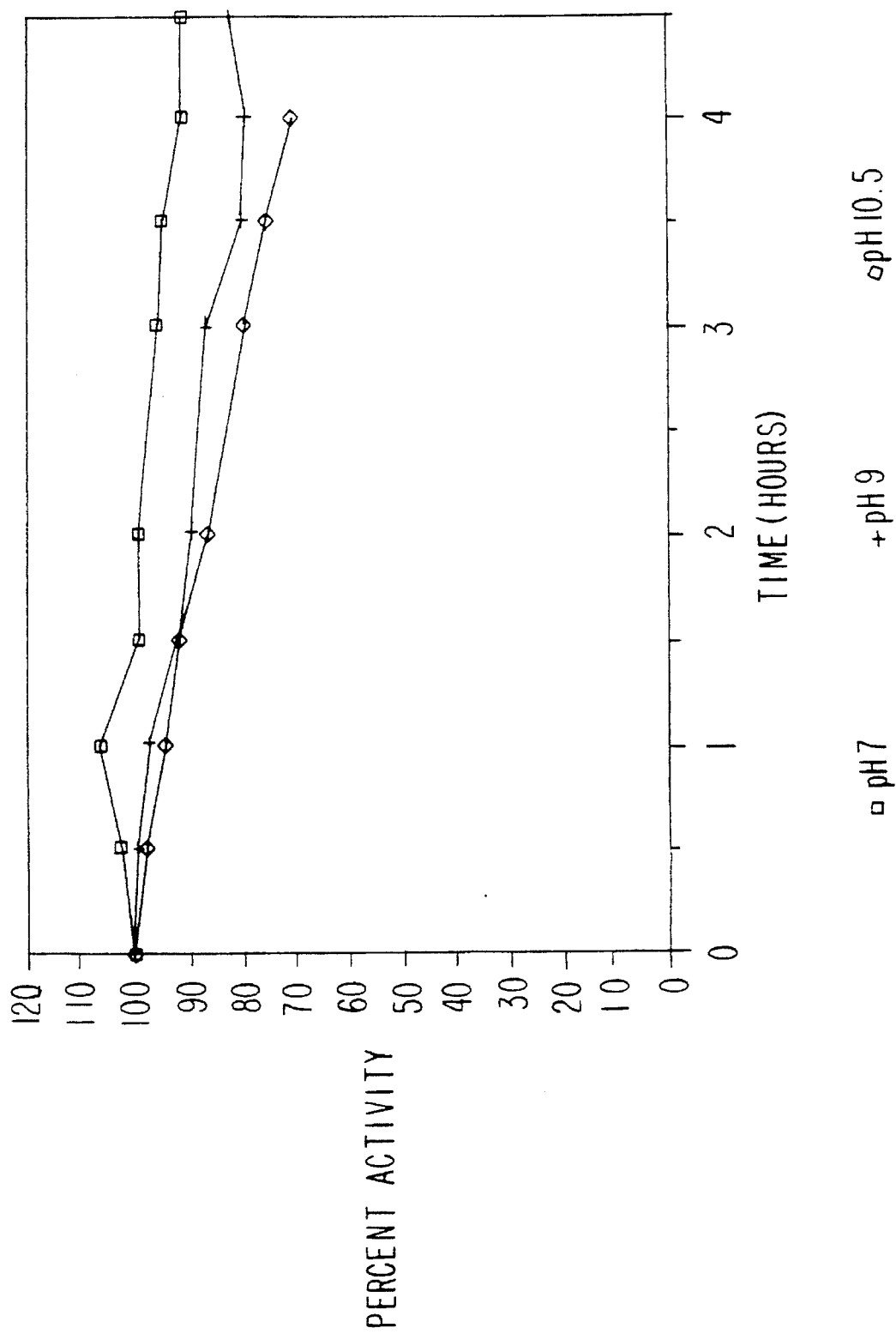

FIG. 15 illustrates the Thermostability of Xylanase (65° C.).

Figure 16:
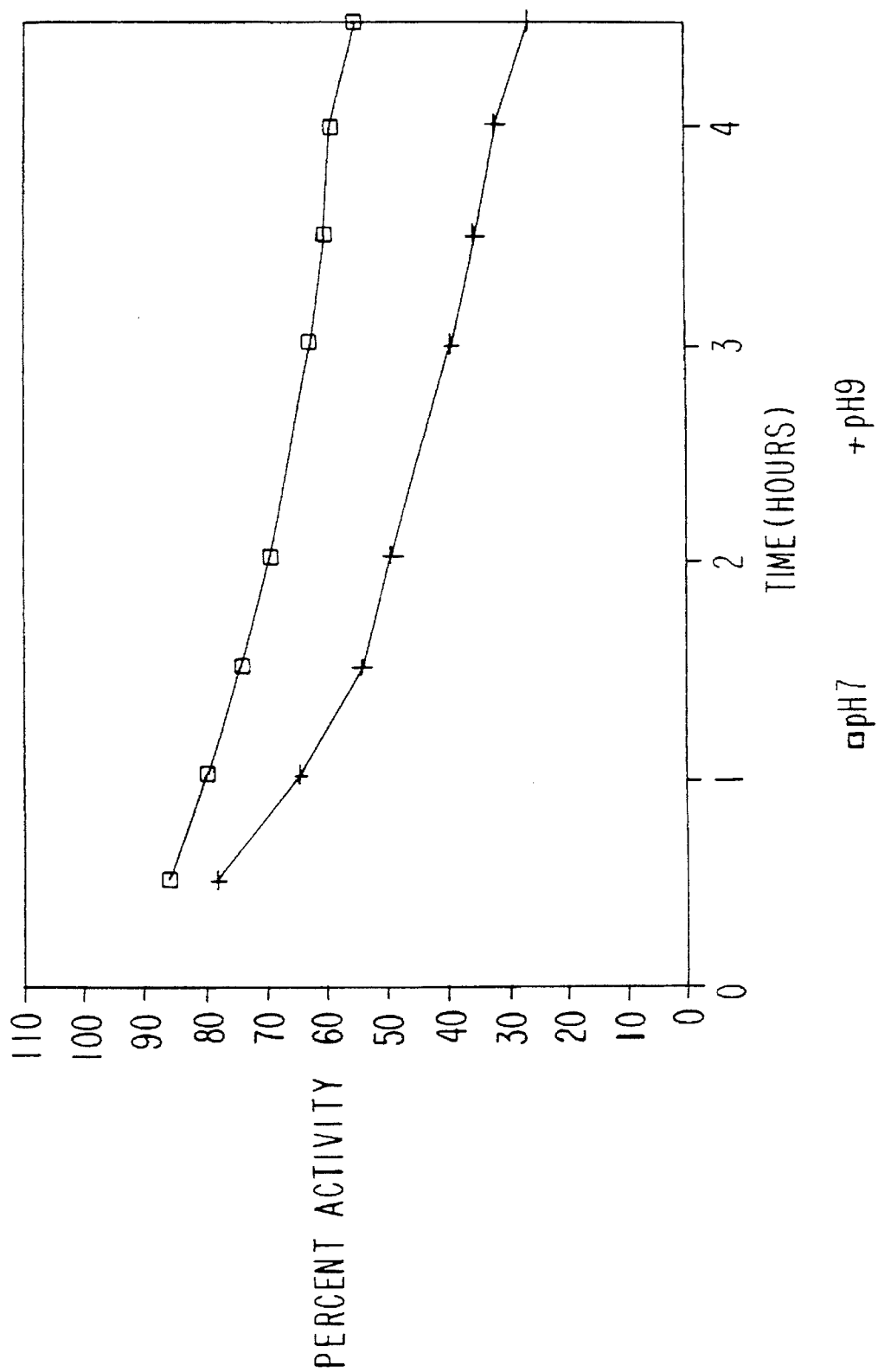

FIG. 16 illustrates the Thermostability of Xylosidase (65° C.).

Figure 17:
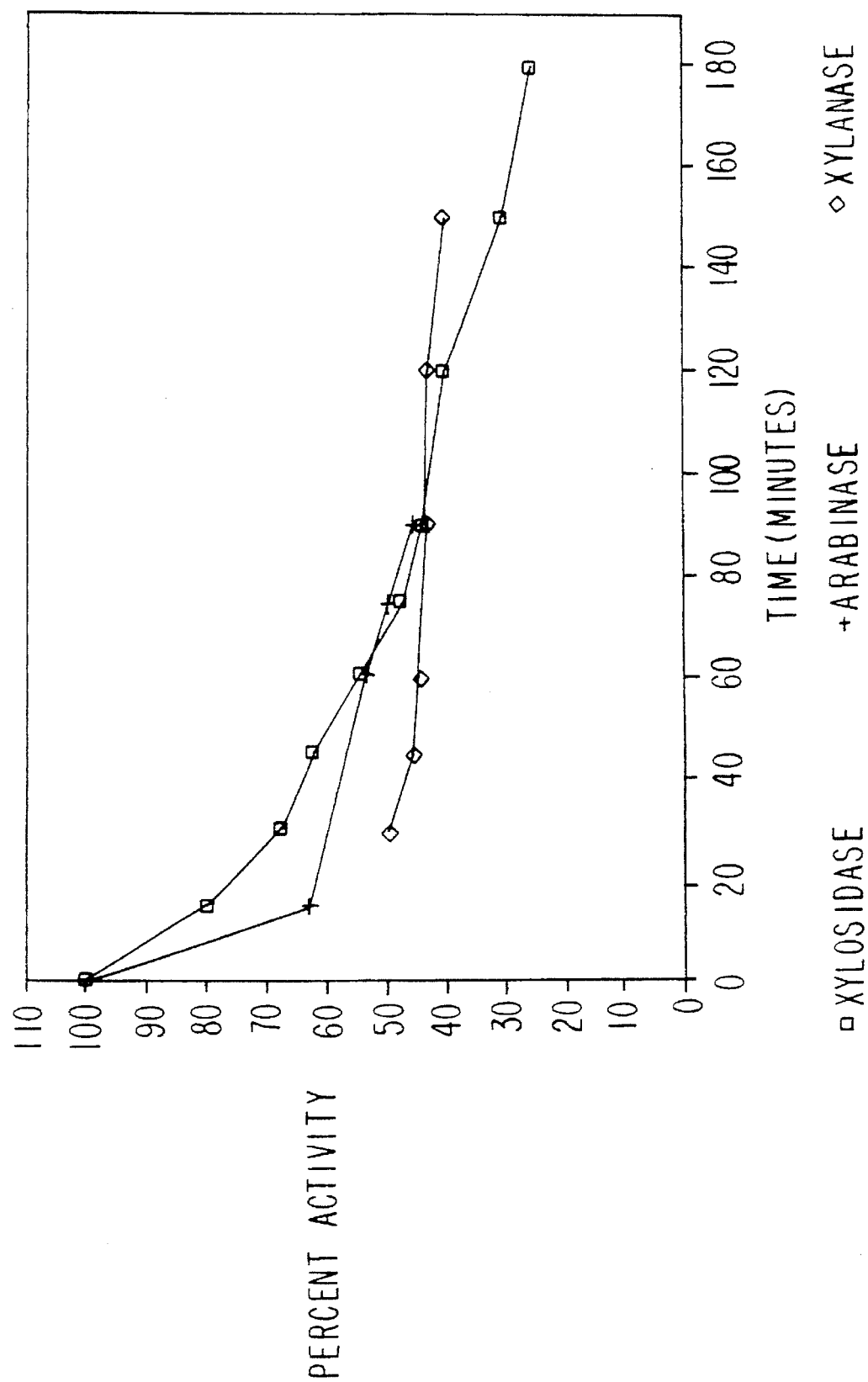

FIG. 17 shows the Thermostability of Xylanase, Xylosidase, Arabinofuranosidase (70° C.).

Figure 18:
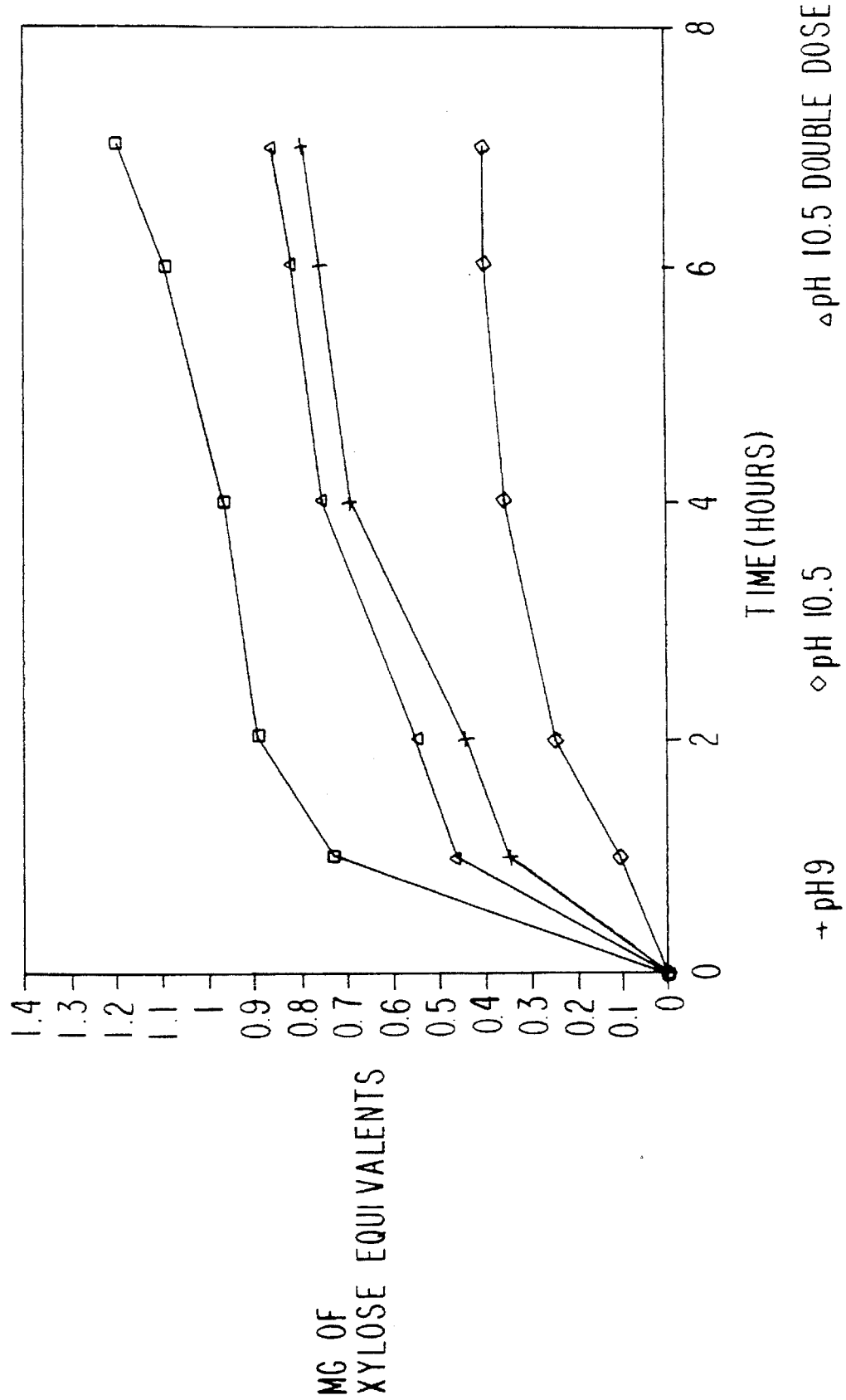

FIG. 18 shows the Hydrolysis of Larchwood Xylan.

Figure 19:
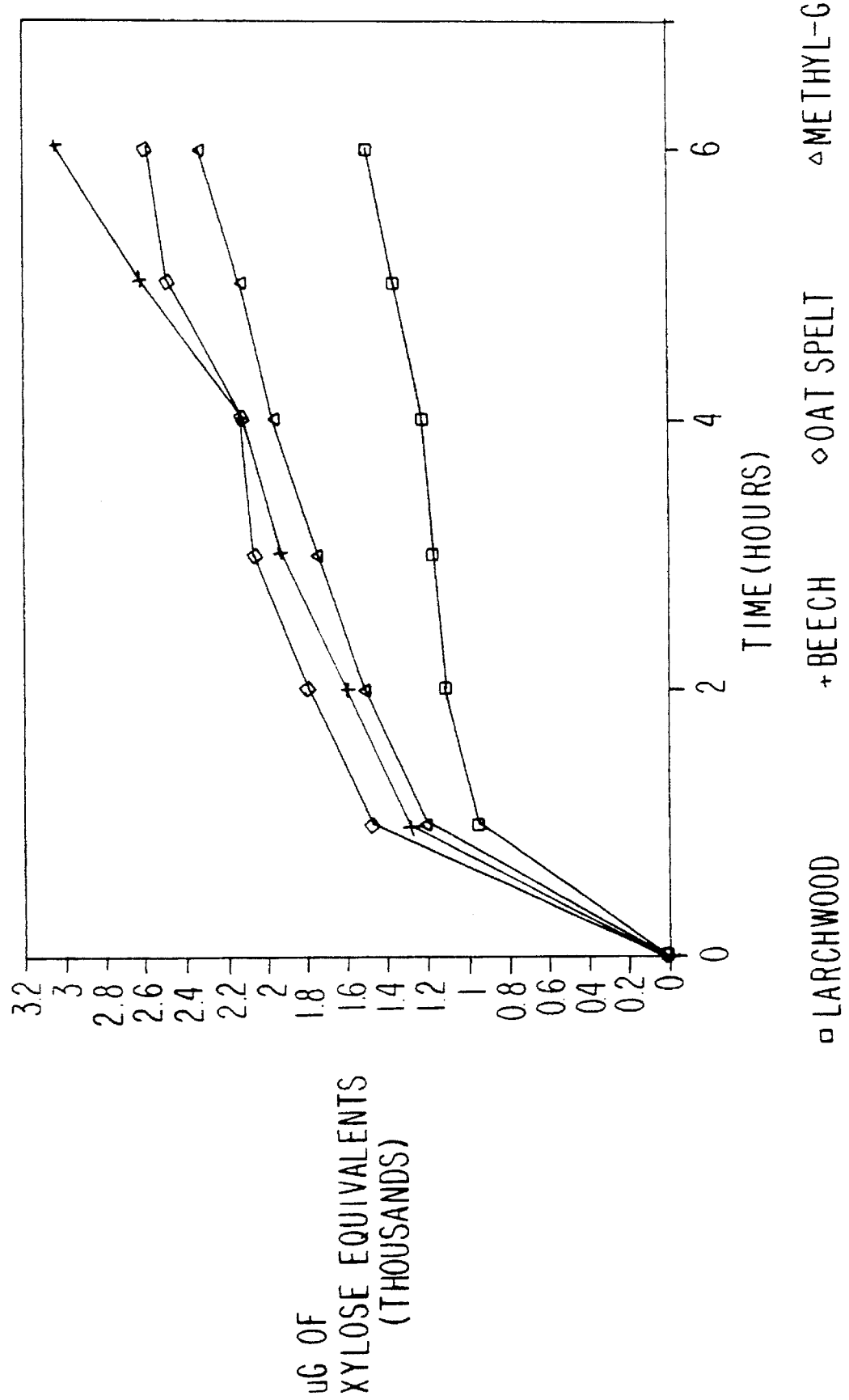

FIG. 19 shows the Hydrolysis of Larchwood, Beech, Oat Spelt and 4-0-Methyl-Glucurono Xylans (pH 7).

Figure 20:
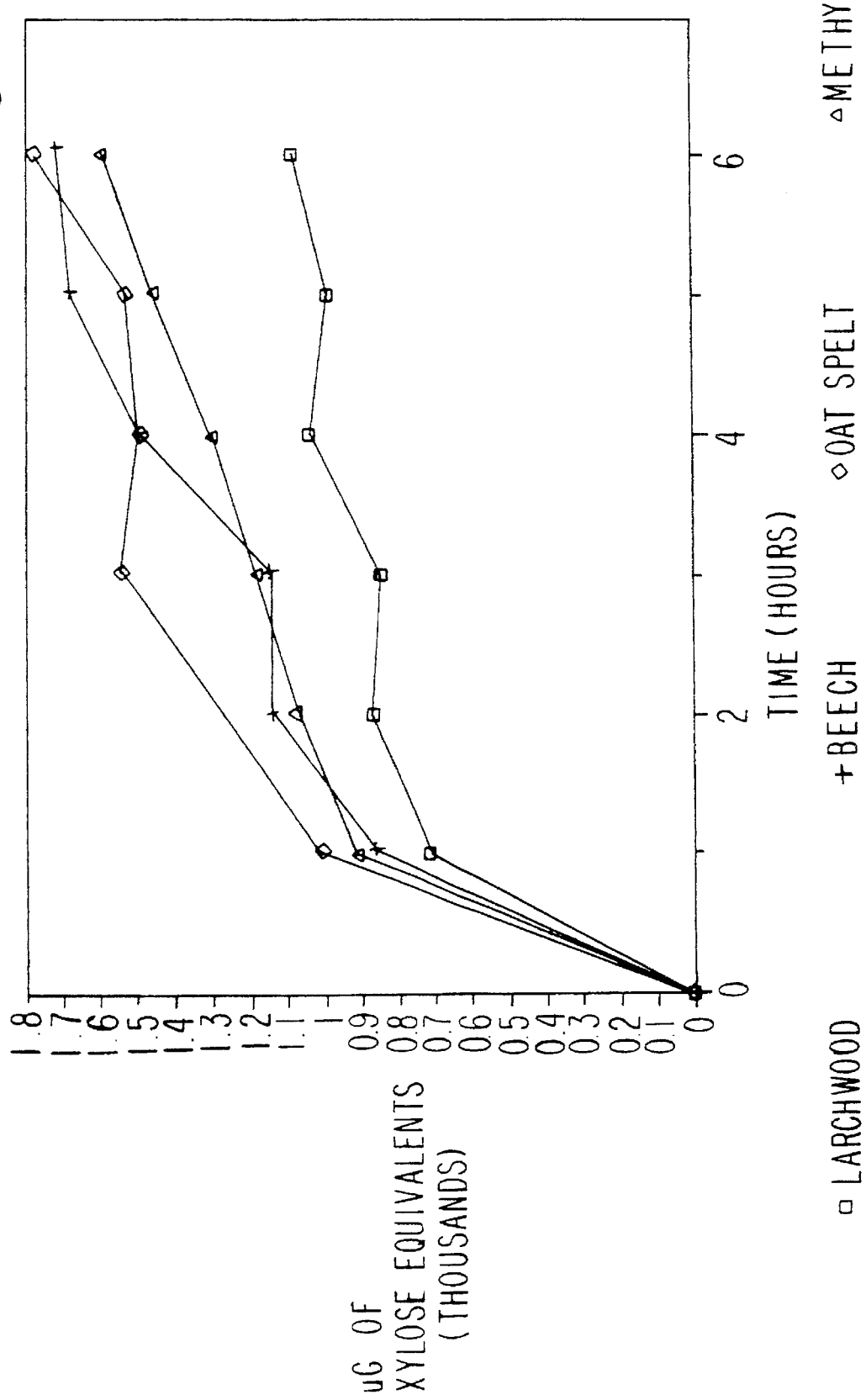

FIG. 20 shows the Hydrolysis of Larchwood, Beech, Oat Spelt and 4-0-Methyl-Glucurono Xylans (pH 9).

Figure 21:
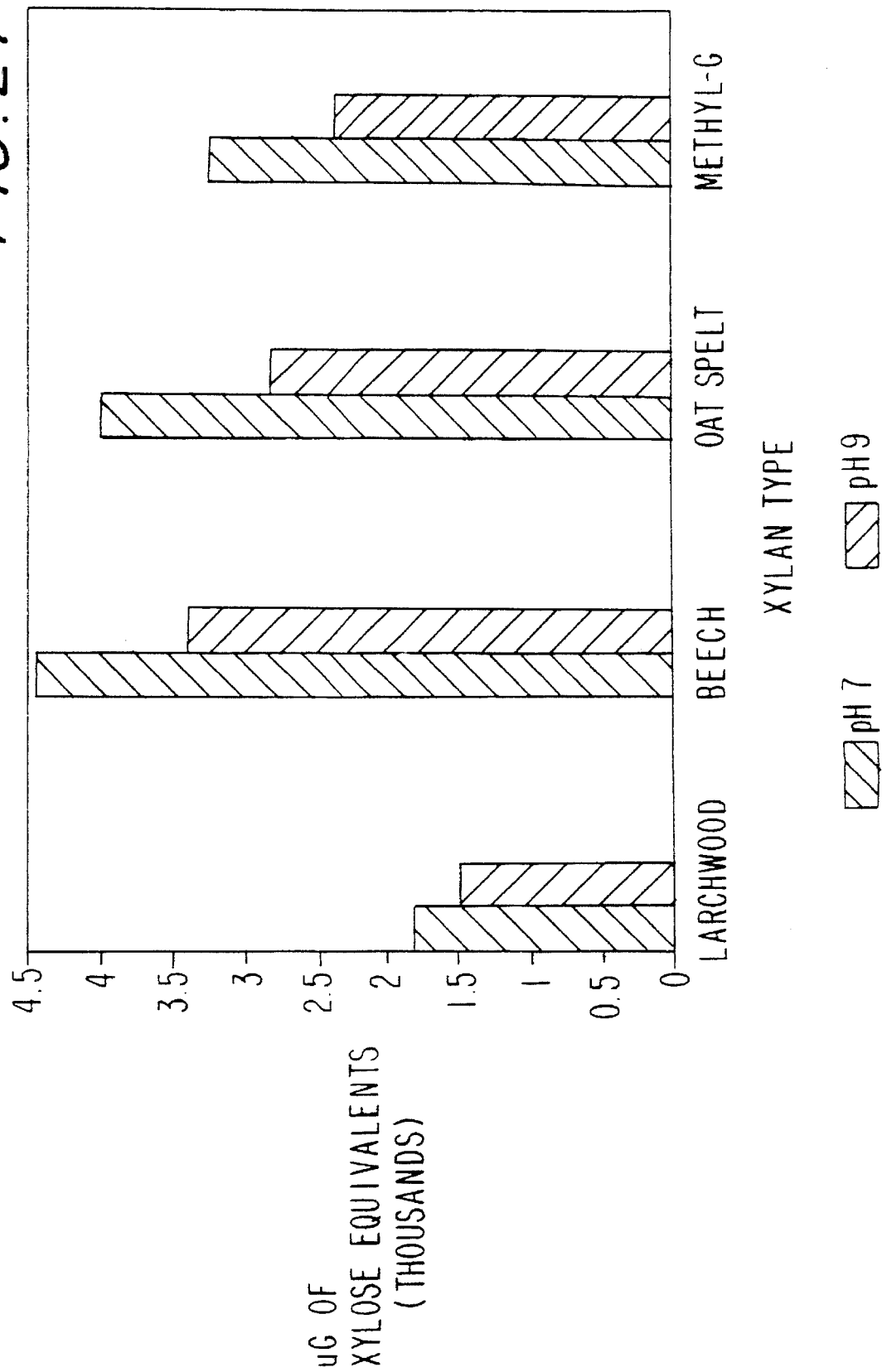

FIG. 21 illustrates the Hydrolysis of Xylans after 23 Hours.

Figure 22:
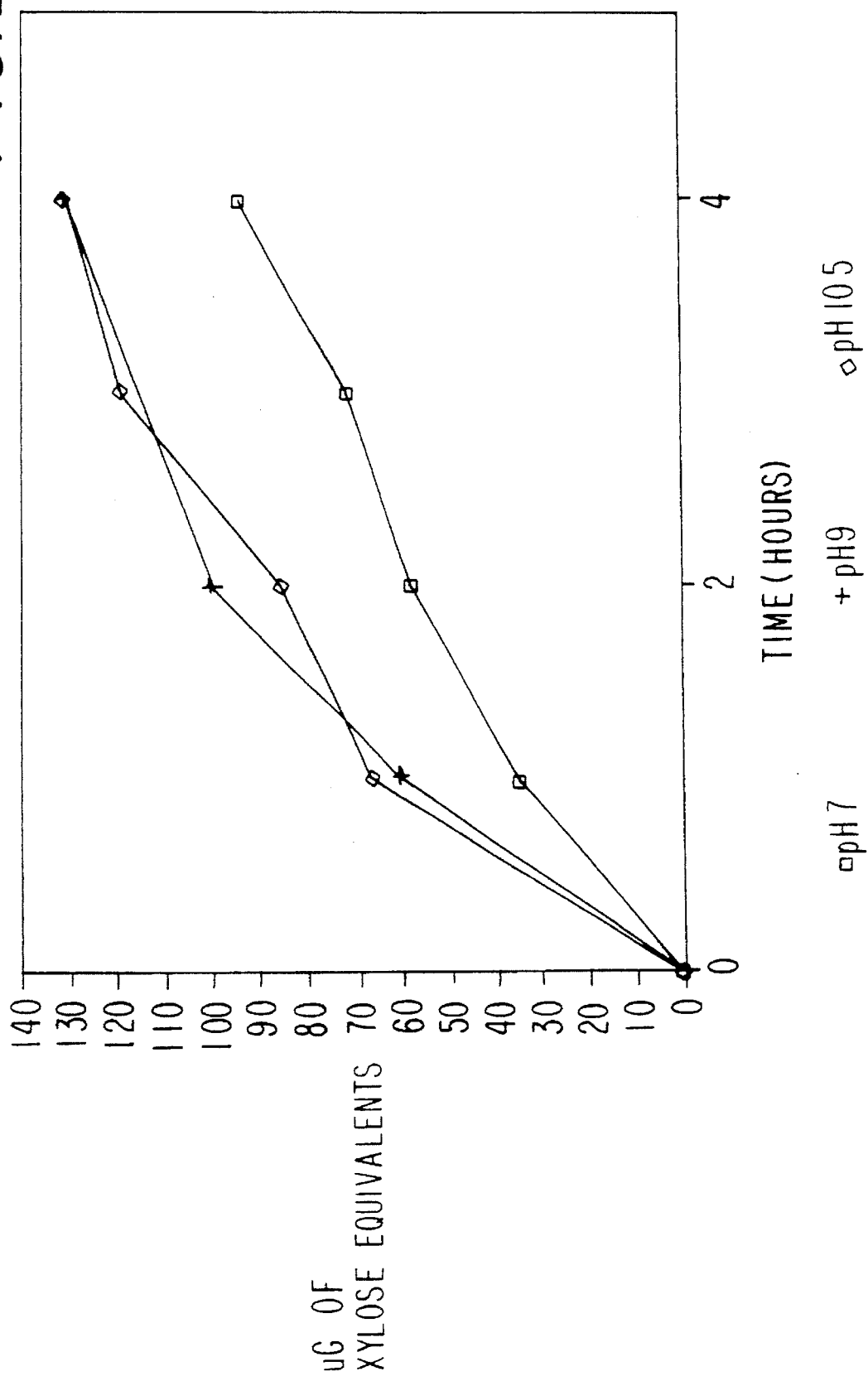

FIG. 22 shows the Hydrolysis of Aspen Wood Pulp.

Figure 23:
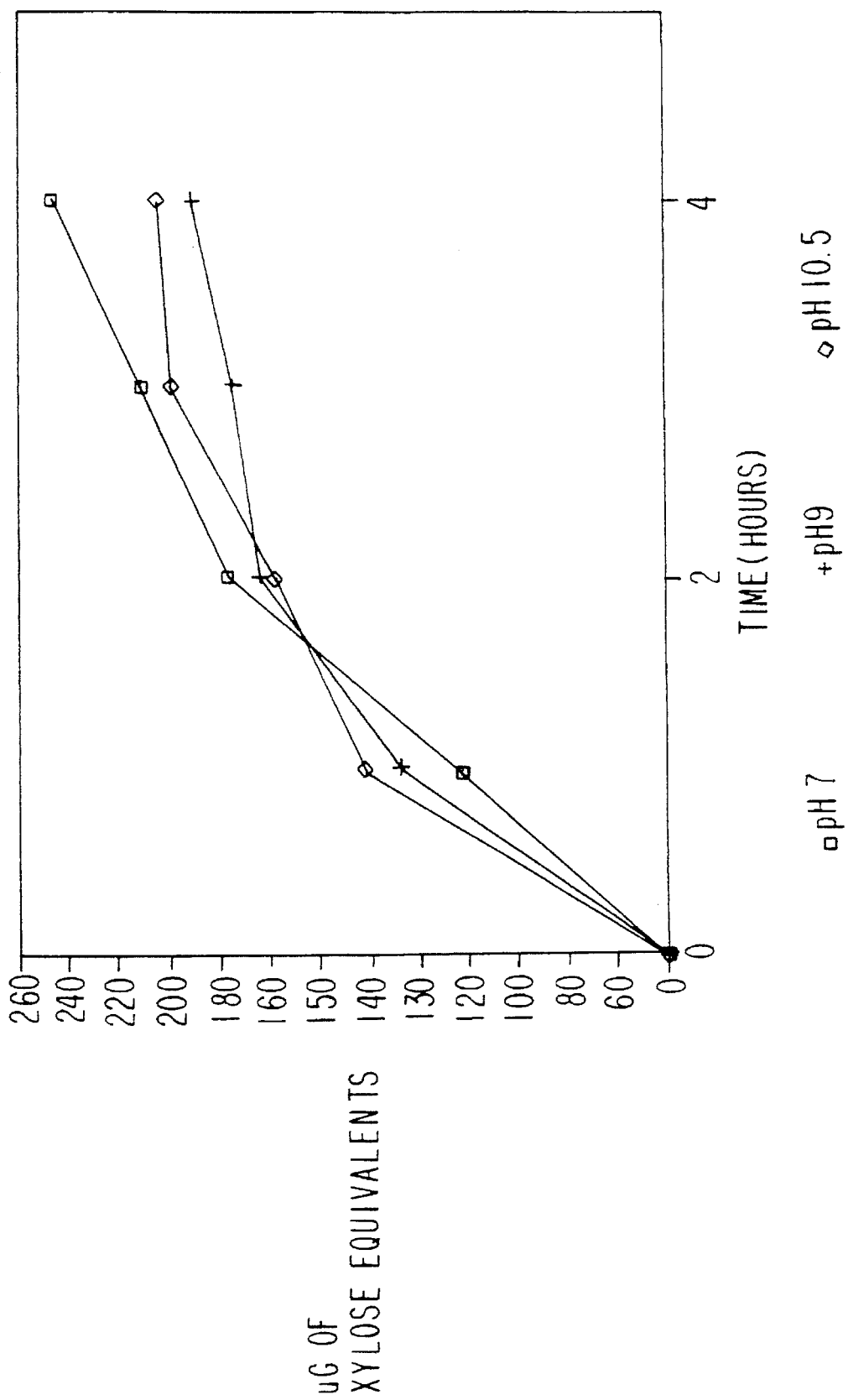

FIG. 23 illustrates the Hydrolysis of Aspen Wood Pulp.

Figure 24:
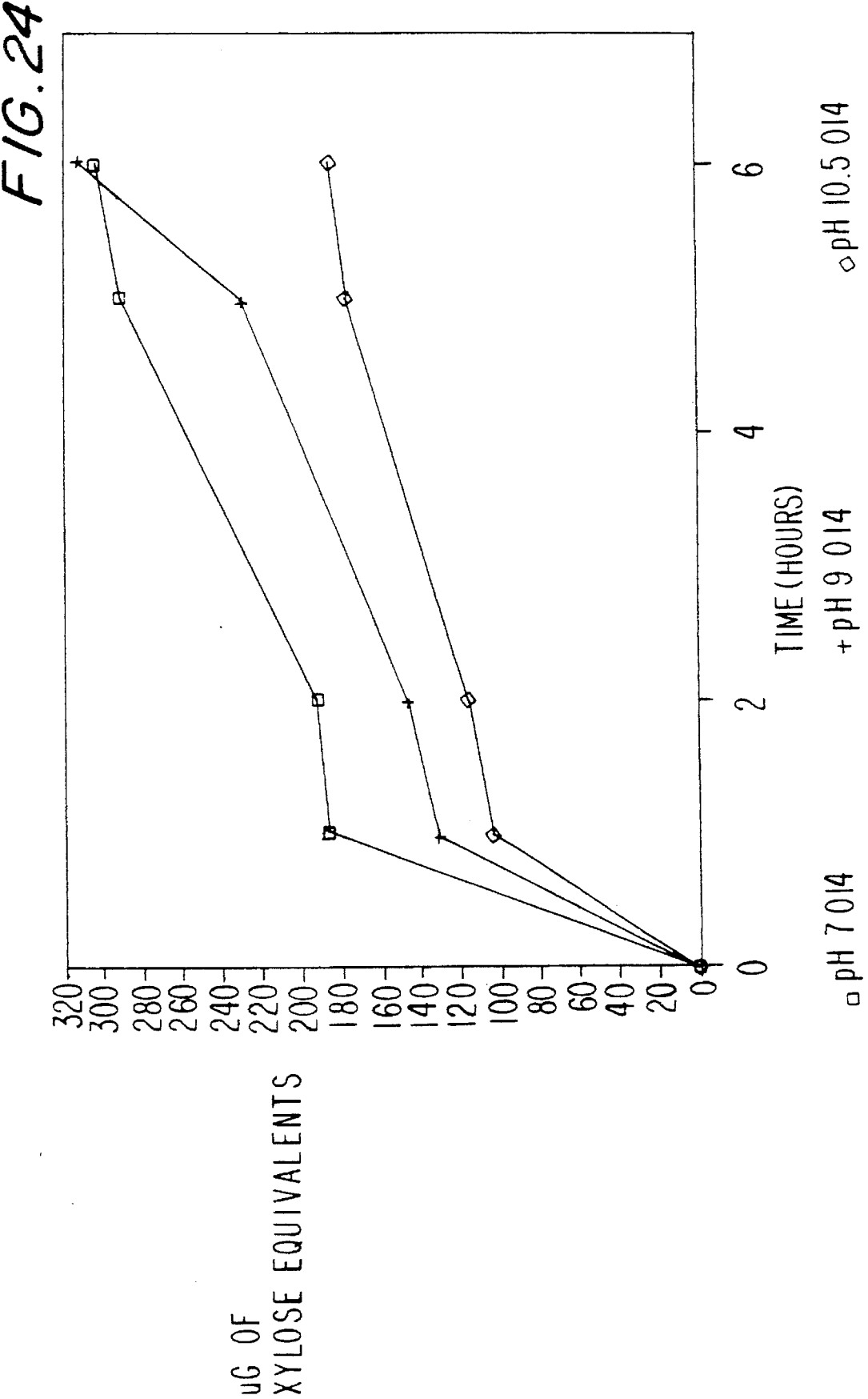

FIG. 24 shows the Hydrolysis of Loblolly Pine Pulp.

Figure 25:
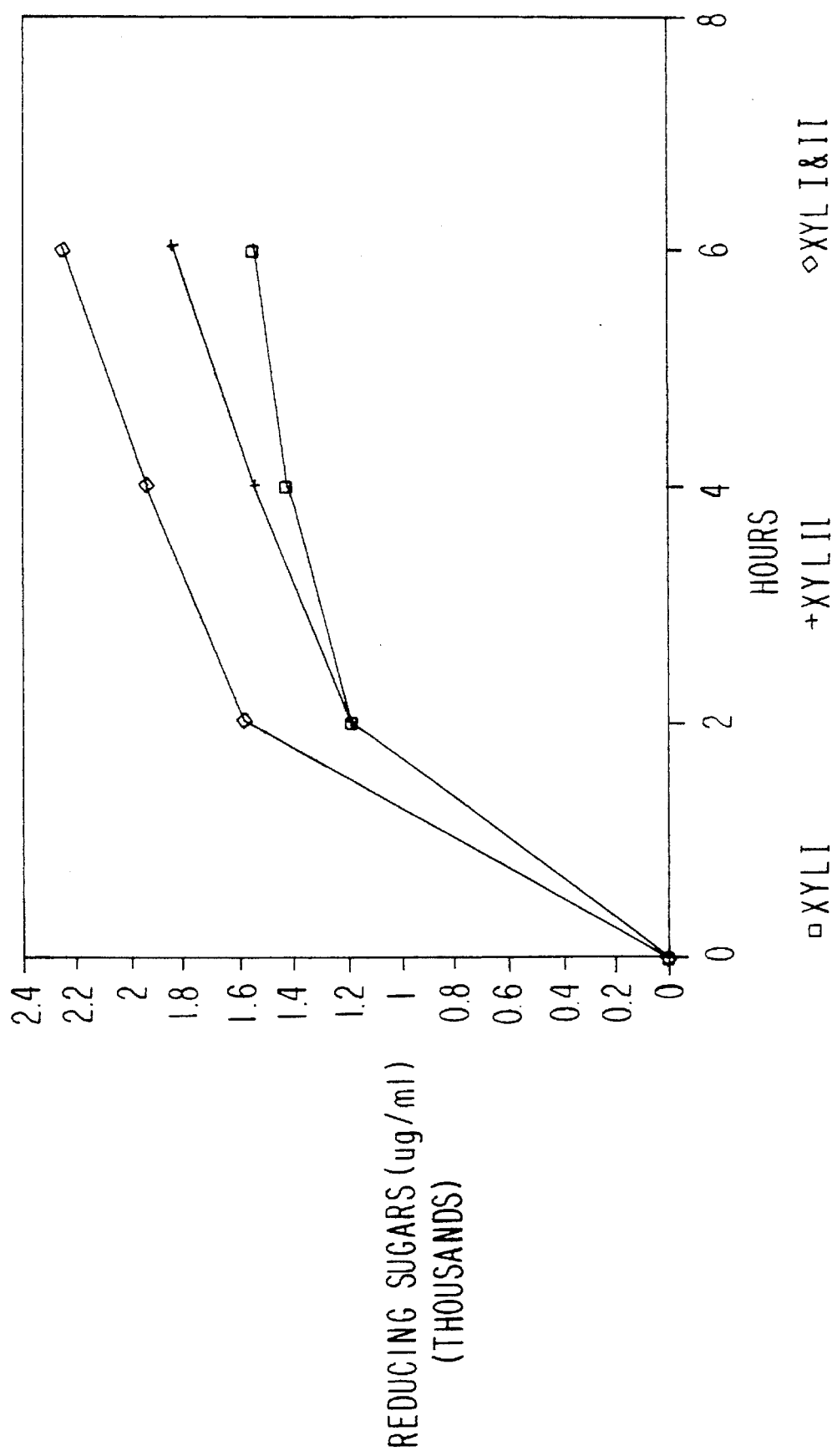

FIG. 25 shows Xylan Hydrolysis with Purified Xylanases.

Figure 26:
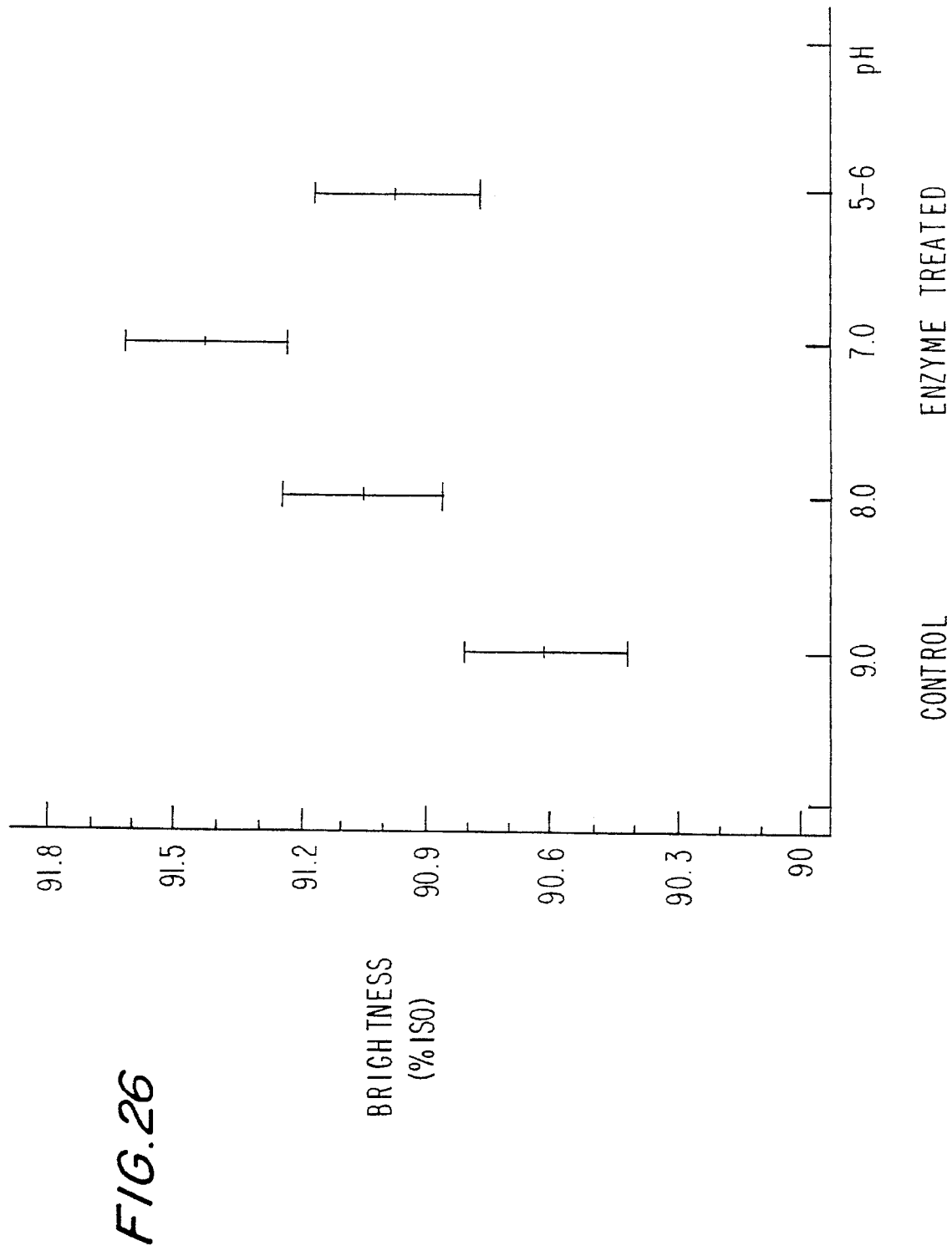

FIG. 26 shows the Brightness of Pulp Treated with Xylanase.

FIG. 27 shows the Effect of Xylanase on CE Kappa Number.

4.0 DETAILED DESCRIPTION OF INVENTION

4.1 Methods for Enzyme Activity Analyses

Xylanase was determined by assaying for reducing sugars released from oat spelt xylan (XIU) or by the release of soluble dyed fragments from Remazol Brilliant Blue xylan (XRU).

4.1.1 XIU Assay

The assay is performed on 1% xylan (Sigma-oat spelt xylan) prepared in 0.1M citrate-phosphate-borate buffer. The assay is run for 20 minutes at 60° C. using 1.0 ml of substrate and 0.5 ml enzyme solution. The assay is stopped after 20 minutes by the addition of 3.0 ml DNS reagent (10 g, 3,5,-dinitrosalicylic acid; 200 g, potassium sodium tartrate; 10 g sodium hydroxide; 0.5 g sodium sulfite; 2.0 g, phenol; in 1 liter of deionized water). The tubes are then boiled for 5 minutes, cooled, and 10.0 ml of water is added and mixed. The absorbance is read on a spectrophotometer at 550 nm and reducing sugars are calculated from a standard curve prepared with xylose (100–800 ug). One XIU is equivalent to 1 micromole of xylose equivalents released from xylan per minute per milliliter or per gram of culture broth.

4.1.2 XRU Assay

This assay is based on the enzymatic release of soluble dyed fragments from soluble xylan, covalently coupled to Remazol Brilliant Blue (RBB) xylan. The substrate can be prepared as described by Biely, et al. [Biely, P., D. Mislovicova, and R. Toman, *Methods in Enzymology* 160 (1988): 536–542.] or can be purchased from Sigma Chemical, St. Louis, Mo. (RBB covalently linked to 4-O-Methyl-glucurono-xylan).

The substrate is dissolved in 0.1M citrate-phosphate-borate buffer, pH 7.0 at a concentration of 6 mg/ml. One ml of the substrate is added to a 10 ml test tube and pre-warmed in a water bath at 60° C. The assay is started by adding 200 ul of enzyme sample to the substrate and incubating 20 minutes. The assay is stopped by the addition of 2.0 ml of 95–100% ethanol. The tubes are mixed, allowed to sit 20 minutes, then aliquots centrifuged.

The absorbance of the ethanol/dye solution is read on a spectrophotometer at 595 nm, blanked with a substrate/water blank (approximately 0.1 ABS). Enzyme activity is expressed as XRU/g, where one XRU is equal to an increase in absorbance of 1.0 O.D. per minute per gram of enzyme.

4.1.3 PNP-X Assay for B-D xylosidase [EC 3.2.1.37]

The substrate for this assay is p-nitrophenol-xylopyranoside (PNP-X) from Sigma. The assay uses 5 mM PNP-X prepared in 0.1M citrate-phosphate-borate buffer, pH 7.0 as the substrate. The assay is performed using 0.9 ml of substrate and 0.1 ml enzyme sample incubated at 60° C. for 20 minutes. The assay and color are developed by the addition of 1 ml of 2M sodium carbonate. The absorbance is read at 410 nm and compared to a standard curve prepared using p-nitrophenol (0–160 uM). One PNP-X unit is equivalent to one micromole of p-nitrophenol or xylose released per minute per gram of enzyme or culture broth.

4.1.4 PNP-A Assay for Alpha-1, 3-Arabinofuranosidase [EC 3.2.1.55]

The substrate for this assay is 2.5 mM p-nitrophenol-arabinofuranoside (PNP-A,Sigma) prepared in 0.1M citrate-phosphate-borate buffer, pH 7.0. The assay is performed using 2.5 mM PNP-A prepared in 0.1M citrate-phosphate-borate buffer, pH 7.0. The assay is performed as described for PNP-X. One PNP-A unit is equivalent to one micromole of P-nitrophenol or arabinose released per minute per gram of enzyme or culture broth.

4.2 Growth of Microorganisms

Strains BPS-3, BPS-3-H-17-4, and 243-7-1 were streaked from frozen stock cultures onto plates of Luria agar tryptone, 10 g/l; yeast extract, 5.0 g/l; $CaCl_2$, 1.0 g/l; and agar 20.0 g/l, pH 7.0], containing 0.1% Remazol Brilliant Blue xylan [Sigma Chemical, St. Louis, Mo.]. The plates were cultured overnight at 55° C. and used to inoculate flasks of medium 162 [see below] containing 0.5% oat spelt xylan or maltodextrin 100. 500 ml baffled flasks containing 100 ml of medium 162 were inoculated with the appropriate strain and grown for 20 hours at 55° C. in an incubator shaker at 250 rpm. The flasks were then used to inoculate fermentation vessels at a level of 5% V/V.

| Medium 162 | |
|---|---|
| yeast extract | 5.0 g/l |
| tryptone | 5.0 g/l |
| $[NH_4]_2SO_4$ | 2.0 g/l |
| $KH_2PO_4$ | 1.1 g/l |
| $Na_2HPO_4$ | 3.4 g/l |
| $CaCl_2.2H_2O$ | 0.3 g/l |
| $MgSO_4.7H_2O$ | 0.3 g/l |
| pH | 7.0 |

4.3 Fermentations

Fermentations were carried out in 2.0 l vessels with a 1.5 l working volume [Multigen, New Brunswick Scientific].

The pH range for xylanase production falls between about 5.5 and 8.0 with the preferred range between 6.5 to 7.5.

The temperature range for growth and production falls between about 45°–65° C., with a preferred range of 50°–60° C.

The time course for production falls between about 5–50 hours with a preferred range of 20–30 hours.

The carbon sources for xylanase production are xylan [oat spelts, beech, larchwood, methyl-glucurono, or arabinoxylan], brewers spent grains, wheat bran, xylose, and maltodextrins. Any combination of above substrates may be used with the preferred mix being xylan and maltodextrin.

Preferred carbon source concentration ranges between about 0.1–2.0% for xylose or xylan, 0.1–1.0% maltrin or spent grains, with the preferred production occurring on 1.0% xylan plus 0.5% maltrin 100.

The nitrogen sources for xylanase production are corn steep liquor, yeast extract, tryptone, hydrolyzed casein, peptone, and ammonium salts. The preferred range for production falls between 0.1–2.0% added nitrogen source.

4.3.1 EXAMPLE 1

Batch fermentations Xyl 011 and 014 were run on the following ingredients:

| | |
|---|---|
| larchwood xylan | 10.0 g/l |
| tryptone [Difco] | 2.5 g/l |
| corn steep liquor | 10.0 g/l |
| yeast extract | 2.5 g/l |
| $KH_2PO_4$ | 0.55 g/l |
| $Na_2HPO_4$ | 1.7 g/l |
| $MgSO_4.7H_2O$ | 0.4 g/l |
| $CaCl_2.2H_2O$ | 0.4 g/l |
| Trace metals AEF-4 | 0.15 ml/l |
| pH controlled with 4N $NH_4OH$ and 10% $H_3PO_4$ | |

The pH of the fermentations were initially set at pH 7.0 and was controlled not to fall below pH 6.5 using 4N $NH_4OH$ or 2M $Na_2CO_3$. The pH was controlled not to rise above 7.5 using 10% $H_3PO_4$. A positive dissolved oxygen tension was maintained throughout the fermentation. The temperature was controlled at 55° C.

Figure 1:
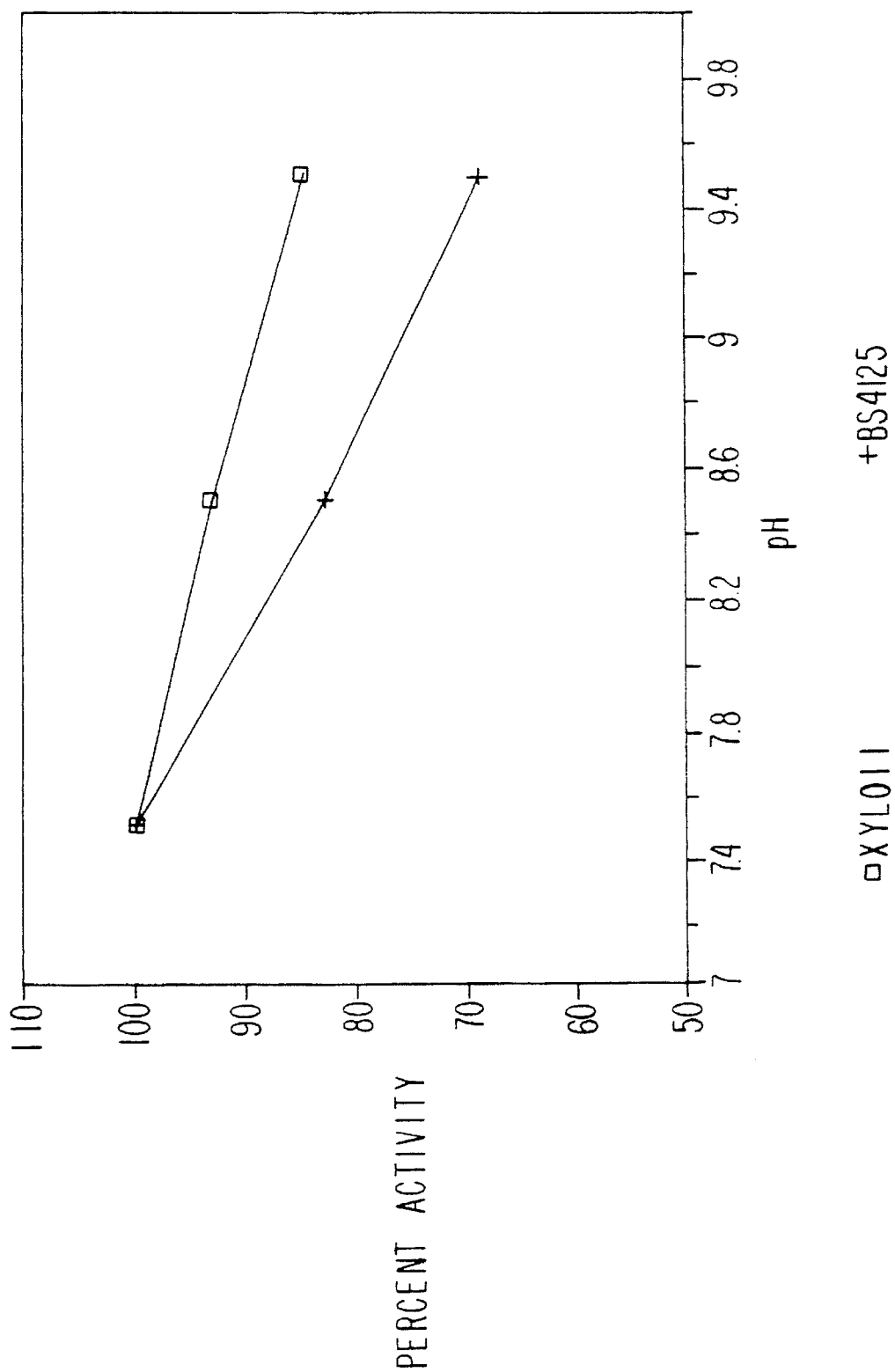
FIG. 1 shows the pH profile of Xyl 011 and BS4125 in Tris Buffer.
Figure 2:
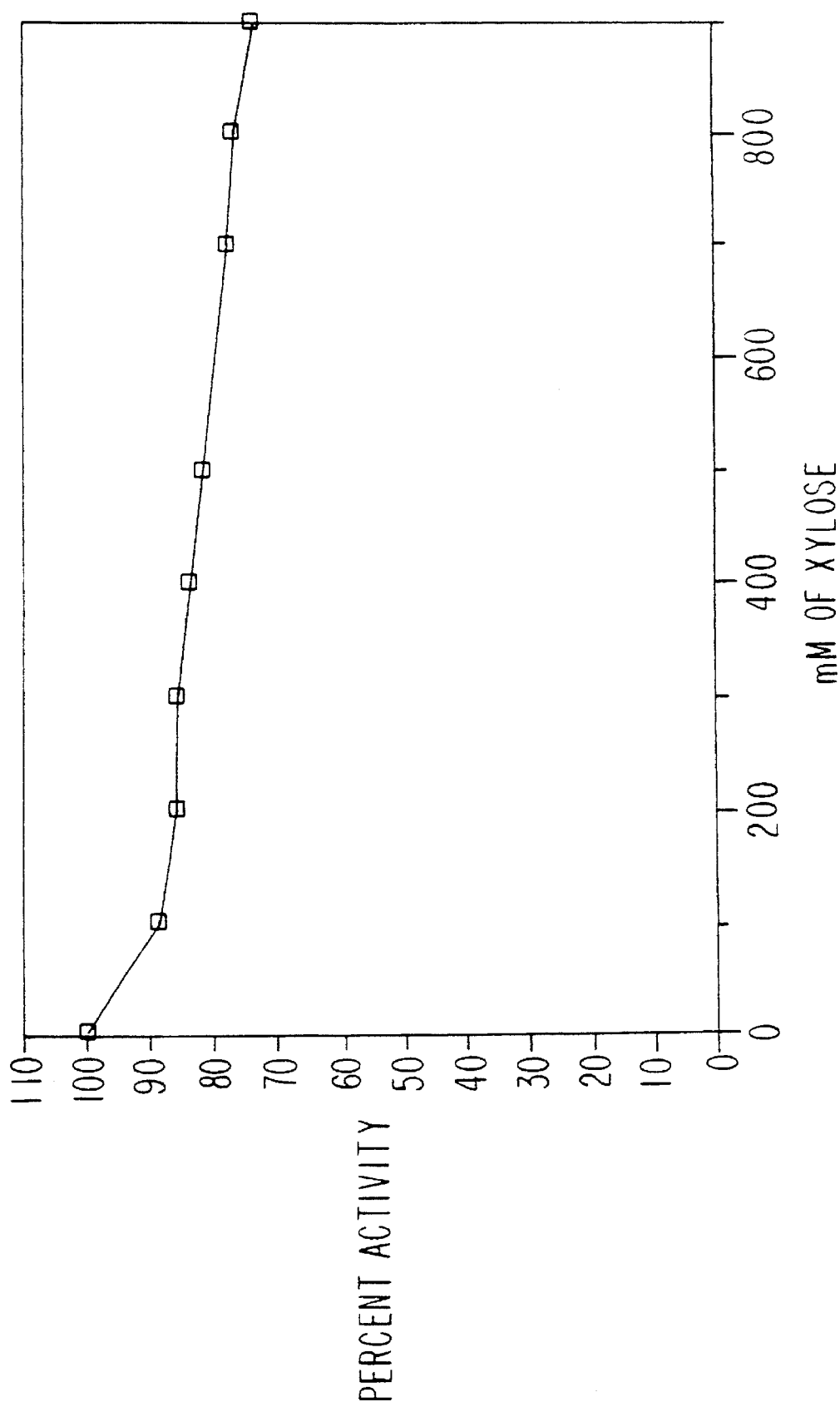
FIG. 2 shows the effect of Xylose on Xylosidase Activity.
Figure 3:
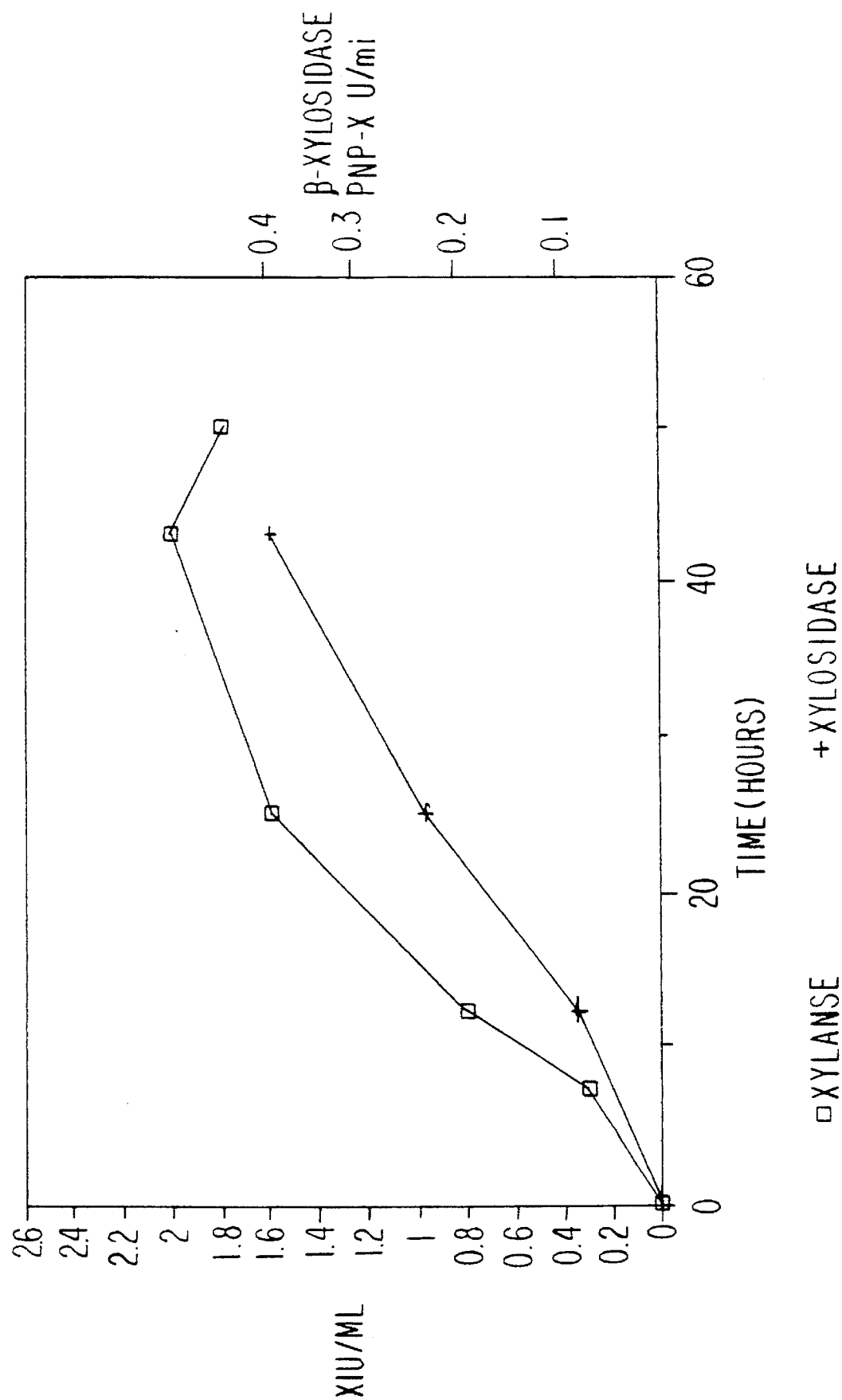
FIG. 3 illustrates Xylanase and Xylosidase Production (BPS-3 H-17-4).

Fermentations Xyl 011 and 014 yielded 2.0 XIU/ml in 44 hours. A plot of Xyl 014 is shown in FIG. 3. The beta-xylosidase level in Xyl 014 reached 0.4 PNP-X U/ml. Both fermentations when harvested showed pH profiles with 60% activity at pH 10.5.

4.3.2 EXAMPLE 2

Batch fermentation Xyl 033 was Dan on the following ingredients:

| | |
|---|---|
| larchwood xylan | 10.0 g/l |
| maltodextrin 100 | 5.0 g/l |
| yeast extract | 5.0 g/l |
| tryptone | 2.0 g/l |
| $[NH_4]_2SO_4$ | 2.0 g/l |
| $Na_2HPO_4$ | 3.4 g/l |
| $KH_2PO_4$ | 1.1 g/l |
| $CaCl_2.2H_2O$ | 0.3 g/l |
| $MgSO_4.7H_2O$ | 0.3 g/l |
| Trace metals AEF-4 | 0.15 ml/l |
| pH controlled with $NH_4$ OH and 10% $H_3PO_4$ | |

The fermentation parameters were set as described for Xyl 011 and 014.

Fermentation Xyl 033 produced 7.0 XIU/ml in 52 hours. The fermentation broth at 20 hours contained 2.0 XIU/ml and showed 60% activity at pH 10.5 as compared to pH 7.0, but by 52 hours the activity at pH 10.5 was only 15%. The production of alkaline xylanase activity appears to be growth associated, while the neutral xylanase activity continues to increase during stationary growth.

4.3.3 EXAMPLE 3

Fed-Batch Fermentation XYL 018. Fed-batch fermentations with BPS-3-H-17-4 were performed using a batch medium containing xylan along with a 50% [W/V%] xylose feed. The pH was controlled not to drop below pH 6.5 using 4N $NH_4OH$. The following ingredients were used:

| | |
|---|---|
| Beech xylan [Lenzig] | 5.0 g/l |
| corn steep liquor | 10.0 g/l |
| yeast extract | 2.0 g/l |
| $[NH_4]_2SO_4$ | 2.0 g/l |
| $K_2HPO_4$ | 2.0 g/l |
| $KH_2PO_4$ | 0.5 g/l |
| $CaCl_2.2H_2O$ | 0.5 g/l |
| $MgSO_4.7H_2O$ | 0.5 g/l |
| Trace metals AEF-4 | 0.15 ml/l |

The feed was started at 22 hours at a constant rate of 3.30 ml/L/hr. The feed was stopped at 90 hours and the fermentation was stopped at 95 hours. A total of 100 g/L of xylose was used. The fermentation yield was 5.0 XRU/ml which is equivalent to about 25–30 XIU/ml. The production of the xylosidase parallels the production of xylanase and a titer of 1.8 PNP-X U/ml was obtained. The yield of the arabinofuranosidase was 0.6 PNP-A U/ml.

Table 1 lists the various enzyme activities in preparations obtained from BPS-3-H-17-4 fermentations. Xyl 011, Xyl 014 and Xyl 022 are lyophilized samples, while Xyl 018 is a liquid prep obtained after ultrafiltration with a 10,000 molecular weight cut off (MWCO) filter and stabilized with 20% sorbitol.

TABLE 1

Enzyme activities of different preparations from BPS-3-H-17-4.

| Prep | XIU/G | XRU/G | PNP-X U/G | PNP-A U/G |
|---|---|---|---|---|
| XYL-011 | 100 | 8.8 | 22.5 | 5 |
| XYL-014 | — | 18.8 | 20.5 | 15 |
| XYL-022 | 630 | 156 | 160 | 75 |
| XYL-018 | 250 | 50 | 13.0 | 4.0 |

This table lists the various preparations used in the experiments shown in this application.

4.3.4 EXAMPLE 4

Culture of Xyl 022. H-17-4, an asporogenous mutant of BPS-3, was grown in a batch fermentation at 55° C. for 48 hours on a medium consisting of oat spelts xylan (5 g/l), beech xylan (5 g/l), 0.1% maltrin-100, and pH controlled to 6.5–7.5 by the addition of 2M sodium carbonate and 10% phosphoric acid.

4.4 Purification

4.4.1 Separation Steps

Steps in the purification of the enzymes described herein preferably include ion-exchange chromatography for an initial separation of differently charged proteins, gel filtration to further purify the enzymes and to obtain molecular weight data, and chromatofocusing to separate proteins with similar pIs. All purification steps were carried out on an FPLC system (Pharmacia) at room temperature. The following procedures were carried out using the culture of Xyl 022 (described in Section 4.3.4 above).

4.4.1.1 Initial Clean-Up

The culture was centrifuged at 8,000 rpm for 20 minutes at 4° C. to remove cells and debris. The supernatant was recovered, concentrated 10-fold with an Amicon PM-10 filter membrane, and dialyzed against 20 mM Tris-HCl, pH 7.0 for 24 hours.

4.3.1.2 Ion-Exchange Chromatography on Mono O 5/5

The concentrated, dialyzed enzyme solution was added to the anion exchange column which was previously equilibrated with 20 mM Tris-HCl, pH 7.0. The alkaline xylanase did not bind to the column matrix (Xylanase I), but the neutral xylanase bound and was eluted by a 0–1M sodium chloride (in buffer) gradient (Xylanase II). The major peak of arabinofuranosidase (arabinase) activity and xylosidase elute from the column well after the xylanase activity. See FIGS. 4 and 5 for a detailed illustration. All the activities were collected separately, concentrated about 5-fold with a Centricon-10 microconcentrator (Amicon) and stored at 4° C.

4.4.1.3 Gel Filtration Chromatography on Superose 6

Once the column was equilibrated in 0.05M sodium phosphate and 0.15M sodium chloride, pH 7.2, the following standards were loaded for calibration: bovine serum albumin (4 mg/ml), ovalbumin (4 mg/ml), carbonic anhydrase (2 mg/ml), and cytochrome C (1.5 mg/ml). Once the calibration was completed, the concentrated samples of Xylanase I and II were separately applied to the column in the same buffer as the standards. The active xylanase fractions from each run were collected and stored at 4° C.

4.4.1.4 Chromatofocusing on Mono P 5/20

Xylanase II, obtained from the ion-exchange step, was applied to the column which was equilibrated in 20 mM bis-Tris, pH 6.4 (Buffer A). Five peaks of xylanase (Xylanase IIa, IIb, IIc, IId, IIe) were eluted by a linear gradient formed by Buffer A and Polybuffer 74 (diluted 1:10 in water, pH 5.0). See FIG. 6 for a diagram of a typical chromatogram.

Table 2 gives details of preferred purification steps.

TABLE 2

| Enzyme Activity | Units | Specific Protein (mg/ml) | Activity (U/g) | % Recovery (Stepwise) |
|---|---|---|---|---|
| Centrifugation: | | | | |
| Crude Xy122 | 102 XRU/ml | 23 | 4.4 | 100 |
| | 32.6 PNP-X/ml | 23 | 1.4 | |
| | 16.2 PNP-A/ml | 23 | 0.7 | |
| Ion-Exchange: | | | | |
| Xylanase I | 0.58 XRU/ml | 0.38 | 1.5 | 3 |
| Xylanase II | 8.2 XRU/ml | 0.31 | 26.5 | 71 |
| Xylosidase | 1.5 PNP-X/ml | 0.16 | 9.4 | 69 |
| Arabinofuranosidase | 1.0 PNP-A/ml | .23 | 4.4 | 63 |
| Gel Filtration: | | | | |
| Xylanase I | 0.025 XRU/ml | .005 | 5.0 | 43 |
| Xylanase II | 0.43 XRU/ml | .010 | 43.4 | 95 |

Table 2 illustrates that the specific activity of Xylanase II increases about 10 fold, with a recovery of 68% of the original activity after two chromatographic steps.

4.4.2 Overlay Methods

4.4.2.1 Xylanase

The detection xylanase in gels is based on the method described by Biely, et al. [Biely, P., D. Mislovicova, and R. Toman, *Methods in Enzymology* 160 (1988): 536–541.] RBB-xylan (150 mg/ml) made up in Britton-Robinson buffer, pH 7.0 and heated to 60° C. A 20 ml solution of 3% agarose in buffer is brought to a boil at which time the RBB-xylan solution is added and mixed thoroughly. The agarose mixture is immediately poured onto a glass plate creating a gel that is approximately 0.075 cm thick. Once set, the gel is used to detect clearing zones in an isoelectric focusing gel (LKB-polyacrylamide gels). The addition of 100 percent ethanol is preferred since it allows for easier visualization of the zones.

4.4.2.2 Xylosidase and Arabinofuranosidase

The detection of xylosidase and arabinofuranosidase is done similarly to the method for xylanase. A 5 mM solution of either PNP-X and PNP-A is made up in 10 mls Britton-Robinson buffer, pH 7.0 and added to 20 mls of 3% agarose in the same buffer. The yellow zones produced may be enhanced by the addition of 2M sodium bicarbonate.

4.4.3 Molecular Properties

4.4.3.1 Xylanases

Xylanase I has a molecular weight (Mw) of 18,000 by gel filtration. Isoelectric focusing on ampholine polyacrylamide gels from LKB (pH range 3.5–9.0) with RBB-xylan overlays shows that its isoelectric point (pI) is close to 8.4.

Xylanase II run on gel filtration has a Mw of 30,000. On SDS-PAGE the sample has a major and minor band at 38,000 and 32,000, respectively. It is unknown which band is responsible for the xylanase activity or if the smaller band is a proteolytic enzyme product of the xylanase. When applied to the chromatofocusing column, Xylanase II was fractionated into five peaks of activity, all having distinct pIs in the range of 4.5 to 5.0.

4.4.3.2 Arabinofuranosidase and Xylosidase

Overlay data shows that the arabinofuranosidase migrates to a pI of 4.4. Two yellow zones appear in the xylosidase lane at 5.3 and 4.6.

See Table 3 for a summary of pI and Mw data for each enzyme.

TABLE 3

| Properties of Enzymes from Xyl 22. | | |
|---|---|---|
| Enzyme | pI | Mw |
| Xylanase I | 8.4 | 18,000[a] |
| Xylanase IIa | | |
| IIb | | |
| IIc | 4.5–5.0 | 30,000[a] |
| IId | | 32,000[b] or 38,000[b] |
| IIe | | |
| Arabinofuranosidase | 4.4 | ND |
| Xylosidase | 5.3, 4.6 | ND |

TABLE 3-continued

Properties of Enzymes from Xyl 22.

| Enzyme | pI | Mw |
| --- | --- | --- |

ND = Not determined
a = Gel filtration data
b = SDS-PAGE data

Xylanase I and Xylanase II differ from each other with respect to isoelectric point (8.4 vs. 4.5–5.0, respectively) and molecular weight (32,000 daltons vs. 18,000 daltons, respectively).

4.5 Properties of Crude and Purified Preparations

4.5.1 EXAMPLE 5

Temperature Profiles: Temperature profiles for XRU, PNP-X and PNP-A activities were determined using the assays described earlier, performed at temperatures ranging from 40°–85° C. All assays were performed for 20 minutes at pH 7.0.

a) Crude: The temperature optimum for the crude xylanase based on the XRU assay is 65° C. [FIG. 7]. The temperature profile was performed with XYL-011 using 20 mg/ml enzyme dissolved in 0.1M citrate phosphate-borate buffer pH 7.0. The enzyme exhibited only 15% activity at 40° C. and was still 40% active at 75° C.

The temperature profiles for the xylosidase and the arabinofuranosidase are shown in FIG. 8. The arabinofuranosidase has a temperature optima of 65° C., while the xylosidase exhibits maximum activity at 75° C. Both enzymes maintain over 40% activity at 80° C. The enzymes were assayed for 20 minutes at pH 7.0.

b) Purified: Temperature profiles for the purified xylanases were obtained using the XRU assay. Xylanase I has a temperature optimum of 75°–80° C., while Xylanase II has an optimum of 60° C. (FIG. 9).

4.5.2 EXAMPLE 6 pH Profile:

a) Crude: The pH profile for crude xylanase activity [Batch XYL-011] were measured by the XIU and XRU assay (FIG. 10). The enzyme, which shows peak activity between pH 7–7.5, has over 40% activity between a pH range of 5.0 to 11.0. The xylanase has approximately 90% activity at pH 9.0 and 58% activity at pH 11.0.

The pH profiles for crude xylanase activity from shake flask containers of BPS-3, BPS-3-H-17-4 and 243-7-1 grown in medium 162 plus 0.5% xylan is shown in FIG. 11. All three strains show over 60% activity at pH 10.5 as compared to activity at pH 7.0.

The Beta-xylosidase and the arabinofuranosidase both show maximum activity at pH 6.0 (FIG. 12 & 13, respectively). The active range of both enzymes is much narrower than the xylanase, exhibiting little activity above pH 9.0.

b) Purified: The pH profiles for Xylanase I and Xylanase II (purified components) are shown in FIG. 14. Xylanase I has optimal activity at pH 7.0 and Xylanase II's optimum is pH 8.0.

4.5.3 EXAMPLE 7

Thermostability: The thermostability of the crude xylanase was measured by the XRU method after preincubation at 65° C. The enzyme [XYL 011] was incubated without the presence of substrate for 4 hours at pH 7, 9 and 10.5. The percent remaining activity versus time is shown in FIG. 15. The enzyme retains 95% activity after 4 hours at pH 7, and retains 90% and 80% activity at pH 9 and 10.5 respectively.

The thermostability of the Beta-xylosidase at 65° C., pH 7 and 9 is shown in FIG. 16. The enzyme has a half-life at pH 9 of 2.5 hours and retains 60% activity after 4.5 hours at pH 7.0.

The thermostability of the xylanase, xylosidase and arabinofuranosidase at 70° C., pH 7.0 is shown in FIG. 17. The xylanase and xylosidase maintain 45% activity after 2 hours, while the arabinofuranosidase has a half-life of 80 minutes under the stated conditions.

4.6 Application

4.6.1 EXAMPLE 8

4.6.1.1 EXAMPLE 8.1

Xylan Hydrolysis-Crude Prep

Initial hydrolysis experiments were performed using larchwood xylan (Sigma) at a concentration of 2.5 mg/ml. The hydrolysis was carried out in 0.1M citrate-phosphate-borate buffer, pH 7, 9 and 10.5, containing 0.05% sodium azide as an anti-microbial agent. 25 mls of enzyme made up to 250 mls in buffer was incubated with the substrate for 24 hours at 60° C., with samples removed at defined intervals. Controls were made up in a similar manner, replacing the enzyme with the same volume of buffer.

Hydrolysis experiments were also performed using 5 mg/ml xylan prepared as described above. For these experiments, latchwood xylan, oat spelt xylan, beechwood xylan, and 4-O-methyl-glucurono-xylan were used. Enzyme from XYL 014 was added at 2 mg/ml buffer. Hydrolysis was performed at 100 rpm, 60° C., for 24 hours.

The XIU assay, described above, was used to determine free reducing sugars.

The hydrolysis of larchwood xylan [2.5 mg/ml] by the crude prep (XYL 011) over time is shown in FIG. 18. The enzyme was dosed a 1 mg/ml [pH 7 and 9] and 2 mg/ml at pH 10.5. After 7 hours, hydrolysis at pH 7.0, 1.25 mg/ml free reducing sugars were obtained [50% hydrolysis].

XYL 011 dosed at 1 mg/ml at pH 10.5 gave approximately 15% hydrolysis, but an increased dose [2 mg/ml] gave 35% hydrolysis. The hydrolysis at pH 9.0 after 7 hours was 30%. The hydrolysis after 24 hours, pH 7.0 reached 85%, while the hydrolysis at pH 9 and 10.5 approached 50%.

The enzyme prep, Xyl 014 (2 mg/ml), hydrolyzed larchwood, oat spelt, beech and 4-0-methyl glucurono xylans (5 mg/ml) at pH 7 and 9 for 24 hours at 60° C. FIGS. 19 and 20 shows the rate of hydrolysis on each substrate at pH 7 and 9 respectively. At pH 7.0, the hydrolysis of beechwood and oat spelts were approximately two-fold higher than at pH 9.0. The hydrolysis of larchwood was not as complete with Xyl 014 (28%) at Xyl 011 (45%) after six hours.

The results obtained after 23 hours of hydrolysis with the 4 xylan substrates is shown in FIG. 21. Hydrolysis of beech xylan approached 86% at pH 7.0 and 70% at pH 9.0.

Hydrolysis of all 4 substrates at pH 9.0 was at least 70% of the reaction obtained at pH 7.0.

4.6.1.2 EXAMPLE 8.2

Wood Pulp Hydrolysis

The hydrolysis of hardwood and softwood pulps and the determination of free pentose sugars released was performed in a similar manner to the xylan hydrolysis experiments. For the experiments, 5 g of pulp, Aspen (20% DS) or Loblolly Pine (25% DS) were added to 50 ml of citrate-phosphate-borate buffer at pH 7, 9, and 10.5.

The buffer contained 0.05% sodium azide as a preservative. Screw cap flasks containing the pulp-buffer mixture were preincubated at 30 minutes at 60° C. before the addition of enzyme. Enzymes (XYL 011 or XYL 014) were dosed at either 1 or 2 mg/ml buffer. Control flasks received water.

The hydrolysis was carried out at 60° C., 100 rpm for 24 hours with aliquots removed at specific time intervals. Soluble xylan was determined as free xylose using a sensitive (2–20 ug) pentose assay that only detects pentose sugars. [Drury, H. F. *Archives Biochem.* 19 (1949): 455–466.]

The Aspen wood hydrolysis results obtained with 1 mg/ml enzyme (FIG. 22) shows an equal amount of xylan liberated at pH 7 and 9, while solubilization at 10.5 was 70% of that obtained at the low pH values.

When the dose of xylanase is increased to 2 mg/ml, we see a proportional increase in xylan released (FIG. 23). The results at pH 9 and 10.5 were comparable, while slightly more xylan was solubilized at pH 7.0.

The hydrolysis of Loblolly Pine with XYL 014 dosed at 2 mg/ml buffer is shown in FIG. 24. The solubilization of xylan at pH 7 and 9 were equal after 6 hours, while at 10.5 only half the xylan solubilized at pH 7 or 9, was obtained. That result is expected since the xylanase only exhibits 60% activity at pH 10.5.

4.6.1.3 EXAMPLE 8.3

Xylan Hydrolysis-Purified Xylanases

Xylan hydrolysis experiments were also carried out using the purified xylanases I and II. For these experiments, 125 ml screw top flasks were prepared containing 25 ml of citrate-phosphate-borate buffer, pH 7.0 plus 10 mg/ml oat spelt xylan. The xylanases were dosed separately at 0.5 XRU/flask (0.2 XRU/ml) and 1.0 XRU/flask (0.4 XRU/ml). Hydrolysis was also performed using the two enzymes in combination, dosed at 1.0 XRU/flask, (0.5 XRU/flask of each enzyme). The hydrolysis was run for 24 hours at 60° C., with agitation set at 150 rpm.

The results of the hydrolysis with the purified enzymes over a six-hour time period is shown in FIG. 25. The increased dose [1.0 XRU/flask] for both enzymes produced slightly higher levels of hydrolysis than the lower dose [0.5 XRU/flask]. The level of hydrolysis using the combination of Xyl I and Xyl II was better than either enzyme alone showing that a synergism exists between the two enzymes.

4.6.2 EXAMPLE 9

Bleach Boosting

Three experiments of enzyme pretreatment of pulp with *B. stearothermophilus* xylanase prior to a three-step bleaching C/D-E-D have been made on oxygen delignified hardwood kraft pulp (Birch).

Enzyme Treatment: The pulps were treated under the following conditions:

pH=5–6, 7 and 9 respectively

Temperature=50° C.

time=3 hours pulp consistency=10% enzyme concentration=0.5 XIU/g dry pulp (Xyl 011)

Pulp and enzyme were mixed by hand in plastic bags and kept at constant temperature on a water bath.

One control experiment was made. The control sample was submitted to the same treatment as described above (at pH 9) but without addition of enzyme.

The pulps were all washed first with hot and then with cold water after the enzyme step.

The kappa-number and yields were determined after the enzyme treatment.

Bleaching: The pulp was bleached in a bleaching procedure using the following doses of active chlorine:

C/D stage: 0.22 times kappa-number of the control

D stage: 1.0% (w/w) $ClO_2$ on pulp DS Brightness and yield of fully-bleached pulp were measured.

Results: The kappa-number of the pulps after the enzyme step are shown in Table 4.

TABLE 4

|  |  | Kappa-number |
|---|---|---|
| control, | pH = 9 | 8.9 |
| enzyme, | pH = 9 | 8.5 |
| " | pH = 7 | 8.9 |
| " | pH = 5–6 | 8.8 |

The brightness of fully-bleached pulps are shown in Table 5.

TABLE 5

|  |  | Brightness % ISO |
|---|---|---|
| control, | pH = 9 | 90.6 |
| enzyme, | pH = 9 | 91.1 |
| " | pH = 7 | 91.4 |
| " | pH = 5–6 | 91.0 |

The brightnesses are plotted with 95% confidence limits in FIG. 26.

Comments: Compared to a control, run at pH=9, the kappa-numbers are not reduced by the enzyme treatment.

Although the kappa-numbers are not reduced, there seems to be a positive effect on the brightness after a three-stage bleaching.

4.6.3 EXAMPLE 10

Effect of Xylanase on the Kappa Number of a Softwood Pulp.

The crude xylanase from batch Xyl-018 was used to pretreat a softwood kraft pulp before a one-step bleaching and extraction stage.

The pulps were treated under the following conditions:

Pulp=Loblolly Pine kraft brownstock initial kappa number=24 pH=8.5

Time=1 hour

Temperature=60° C.
Pulp Consistency=3.5%
Enzyme Batch=Xyl 018
Dose=12.5 XIU/g OD Pulp Pulp and enzyme were mixed by hand in plastic bags and kept at constant temperature in a water bath. A control sample was submitted to the same treatment as described above, but without addition of enzyme.

The results, shown in FIG. 27, show that the enzyme treatment at an alkaline pH [8.5] and at a kappa factor of 0.14, caused a significant drop in kappa number as compared to the control.

The kappa number of the enzyme treated pulp was reduced to 7.5 at a kappa factor of 0.14 and to 6.6 at a kappa factor of 0.18, while at a 0.14 kappa factor, the control had a kappa number of 14.16 and only dropped 7.12 at a kappa factor of 0.22. The enzyme treatment cut the amount of chlorine needed [kappa factor] to decrease the kappa number to 7.1–7.5 by approximately 70%. (See Table 6.)

TABLE 6

|  | CE KAPPA NUMBER | |
| --- | --- | --- |
| KAPPA FACTOR | ENZYME | NO ENZYME |
| XYL-018 (5% w/w) 0.11 | 12.53 | 17.22 |
| pH 8.5, 60° C., 60 min. 0.14 | 7.50 | 14.16 |
| 0.18 | 6.66 | 10.10 |
| 0.22 | 5.98 | 7.12 |

4.7 Deposit of Microorganisms

The strains have been deposited under conditions that assure that access to the culture will be available during the pendency of this patent application to one determined by the Commissioner of Patents and Trademarks to be entitled thereto under 37 C.F.R. §1.14 and 35 U.S.C. §122 and under conditions of the Budapest Treaty. The deposit represents a biologically pure culture of each deposited strain.

The following microorganisms as described herein have been deposited with the Agricultural Research Culture Collection (NRRL), Peoria, Ill. on Jun. 18, 1990 and have been aligned the following accession numbers:

| Microorganism | Accession Numbers |
| --- | --- |
| BPS-3 | NRRL-B-18659 |
| BPS-3-X2 | NRRL-B-18660 |
| 243-7-1 | NRRL-B-18661 |

The present invention is not to be limited in scope by the microorganisms deposited, since the deposited embodiments are intended as single illustrations of one aspect of the invention and any which are functionally equivalent are within the scope of this invention. Indeed, various modifications of the invention in addition to those shown and described herein will become apparent to those skilled in the art from the foregoing description and accompanying Figures. Such modifications are intended to fall within the scope of the appended claims.

We claim:

1. An isolated arabinofuranosidase having the following characteristics:

(a) has a maximum activity at about pH 6.0;

(b) has a maximum activity at about 65° C.;

(c) maintains at least about 50% of its maximum activity at about 70° C. and pH 7 after 80 minutes;

(e) has an isoelectric point of about 4.4; and (f) is obtainable from a strain of *Bacillus stearothermophilus* selected from the group consisting of *Bacillus stearothermophilus* NRRL B-18659, *Bacillus stearothermophilus NRRL B*-18660, and *Bacillus stearothermophilus* NRRL B-18661.

2. The isolated arabinofuranosidase of claim 1 in which said xylosidase is produced by *Bacillus stearothermophilus* NRRL B-18659.

3. The isolated arabinofuranosidase of claim 1 in which said xylosidase is produced by *Bacillus stearothermophilus* NRRL B-18660.

4. The isolated arabinofuranosidase of claim 1 in which said xylosidase is produced by *Bacillus stearothermophilus* NRRL B-18661.

* * * * *